(12) United States Patent
Michelet et al.

(10) Patent No.: US 7,320,967 B2
(45) Date of Patent: Jan. 22, 2008

(54) COSMETIC COMPOSITION, METHOD OF COSMETIC TREATMENT AND PREPARATION OF A COMPOSITION FOR PROMOTING THE GROWTH AND/OR PREVENTING OR DELAYING THE LOSS OF HAIR

(75) Inventors: Jean-François Michelet, Creteil (FR); Bruno Bernard, Neuilly sur Seine (FR); Roger Rozot, Lagny/Marne (FR); Christophe Boulle, Lagny S/Marne (FR)

(73) Assignee: L'Oreal, Paris (FR)

( * ) Notice: Subject to any disclaimer, the term of this patent is extended or adjusted under 35 U.S.C. 154(b) by 328 days.

(21) Appl. No.: 10/420,831

(22) Filed: Apr. 23, 2003

(65) Prior Publication Data

US 2004/0052760 A1 Mar. 18, 2004

Related U.S. Application Data

(60) Provisional application No. 60/425,330, filed on Nov. 12, 2002, provisional application No. 60/387,420, filed on Jun. 11, 2002.

(30) Foreign Application Priority Data

Apr. 23, 2002 (FR) ................................. 02 05067
Oct. 28, 2002 (FR) ................................. 02 13461

(51) Int. Cl.
*A61K 31/675* (2006.01)
*A61K 31/655* (2006.01)
*A61K 8/18* (2006.01)
*A01N 25/34* (2006.01)
*C12N 9/99* (2006.01)

(52) U.S. Cl. ................... 514/91; 514/157; 424/70.1; 424/408; 435/184

(58) Field of Classification Search ................ 435/184, 435/189; 514/91, 157, 80; 424/408, 59, 424/70.1
See application file for complete search history.

(56) References Cited

U.S. PATENT DOCUMENTS 4,085,111 A 4/1978 Oe et al.
5,030,442 A * 7/1991 Uster et al. .................... 424/45
6,414,027 B1 7/2002 Neal
6,642,274 B1 * 11/2003 Neal ........................... 514/573

FOREIGN PATENT DOCUMENTS

| BE | 888 694 A | 8/1981 |
|---|---|---|
| EP | 0 028 525 A2 | 5/1981 |
| EP | 0 722 715 A1 | 7/1996 |
| WO | WO 9304052 A1 * | 3/1993 |
| WO | 01/01997 A1 | 1/2001 |
| WO | WO 01/55123 A1 | 8/2001 |

OTHER PUBLICATIONS

Craig et al. "Modern Pharmacology" (1990) Third edition, (Little, Brown: Boston, MA). p. 89.*
Watanabe et al. "NADP-linked 15-hydroxyprostglandin dehydrogenase for Prostaglandin D2 in human blood platelets" Arch. Biochem. Biophys. (1982) 216(1): 372-379.*
Abstract—XP 002228469, Database Caplus, Chemical Abstracts Service, Columbus, Ohio, US., Accession No. 2000:573631 & WO 00/47172 A, (Taisho Pharmaceutical Co.) Aug. 17, 2000.
Abstract—XP 002228470, Database Caplus, Chemical Abstracts Service, Columbus, Ohio, US., Accession No. 1978:116914.
Abstract—XP 002228471, Database Chemcats, Accession No. 2001:2149678.
Abstract—XP 002254385, Database Chemcats, Accession No. 2002:2034935.
Abstract—XP 002254386, Database Chemcats, Accession No. 2002:2034929.
Abstract—XP 002254387, Database Chemcats, Accession No. 2002:579734.
Abstract—XP 002254388, Database Chemcats, Accession No. 2001:641048.
French Search Report Corresponding to FR 02/13461 issued on Sep. 12, 2003, 2 Pages.
International Search Report Corresponding to PCT/FR 03/01285 Issued on Sep. 12, 2003, 4 Pages.

* cited by examiner

*Primary Examiner*—Leon B. Lankford, Jr.
*Assistant Examiner*—Susan Hanley
(74) *Attorney, Agent, or Firm*—Buchanan, Ingersoll & Rooney, PC

(57) ABSTRACT

The invention relates to a cosmetic composition containing at least one 15-hydroxy-prostaglandin dehydrogenase inhibitor and cosmetically acceptable excipients. It also relates to a method of cosmetic treatment for promoting the growth and/or preventing or delaying the loss of hair, and the use of a 15-hydroxyprostaglandin dehydrogenase inhibitor for the preparation of a composition intended for controlling hair loss and/or for promoting hair regrowth.

52 Claims, 3 Drawing Sheets

Sample 3

SEQUENCE LISTING

<160> NUMBER OF SEQ ID NOS: 10

<210> SEQ ID NO 1
<211> LENGTH: 23
<212> TYPE: DNA
<213> ORGANISM: Homo sapien

<400> SEQUENCE: 1
atggatgatg atatcgccgc gct                                      23

<210> SEQ ID NO 2
<211> LENGTH: 23
<212> TYPE: DNA
<213> ORGANISM: Homo sapien

<400> SEQUENCE: 2
cggactcgtc atactcctgc ttg                                      23

<210> SEQ ID NO 3
<211> LENGTH: 24
<212> TYPE: DNA
<213> ORGANISM: Homo sapien

<400> SEQUENCE: 3
tgccaatgga ttgataacac tcat                                     24

<210> SEQ ID NO 4
<211> LENGTH: 24
<212> TYPE: DNA
<213> ORGANISM: Homo sapien

<400> SEQUENCE: 4
acagcagttt tcatctggga tatg                                     24

<210> SEQ ID NO 5
<211> LENGTH: 19
<212> TYPE: DNA
<213> ORGANISM: Artificial Sequence
<220> FEATURE:
<223> OTHER INFORMATION: Prostaglandin F synthase (PGFS)

<400> SEQUENCE: 5
aattccgggc agcaaacat                                           19

<210> SEQ ID NO 6
<211> LENGTH: 23
<212> TYPE: DNA
<213> ORGANISM: Artificial Sequence
<220> FEATURE:
<223> OTHER INFORMATION: Prostaglandin F synthase (PGFS)

```
<400> SEQUENCE: 6
acacacaggg cttctggtag aca                                          23

<210> SEQ ID NO 7
<211> LENGTH: 29
<212> TYPE: DNA
<213> ORGANISM: Artificial Sequence
<220> FEATURE:
<223> OTHER INFORMATION: primers for 15-PGDH

<400> SEQUENCE: 7
ggggatccat gcacgtgaac ggcaaagtg                                    29

<210> SEQ ID NO 8
<211> LENGTH: 22
<212> TYPE: DNA
<213> ORGANISM: Artificial Sequence
<220> FEATURE:
<223> OTHER INFORMATION: primers for 15-PGDH

<400> SEQUENCE: 8
tctcgagagc tgttcattgg gt                                           22

<210> SEQ ID NO 9
<211> LENGTH: 30
<212> TYPE: DNA
<213> ORGANISM: Artificial Sequence
<220> FEATURE:
<223> OTHER INFORMATION: primers for PGFS

<400> SEQUENCE: 9
cgggatccat ggattccaaa cagcagtgtg                                   30

<210> SEQ ID NO 10
<211> LENGTH: 24
<212> TYPE: DNA
<213> ORGANISM: Artificial Sequence
<220> FEATURE:
<223> OTHER INFORMATION: primers for PGFS

<400> SEQUENCE: 10
cggaattctt aatattcatc tgaa                                         24
```

COSMETIC COMPOSITION, METHOD OF COSMETIC TREATMENT AND PREPARATION OF A COMPOSITION FOR PROMOTING THE GROWTH AND/OR PREVENTING OR DELAYING THE LOSS OF HAIR

CROSS-REFERENCE TO RELATED APPLICATION

This application claims benefit under 35 U.S.C. §119(e) of U.S. Provisional Application No. 60/387,420 filed Jun. 11, 2002 and of U.S. Provisional Application No. 60/425,330, filed Nov. 12, 2002.

The present invention relates to the use of compounds for the preparation of compositions intended for inducing or stimulating the growth of keratinous fibres and in particular human hair and eyelashes. The invention relates to novel compositions for controlling hair loss and/or promoting hair regrowth. It also relates to a method of cosmetic treatment for controlling the loss of keratinous fibres, such as hair or eyelashes, and/or promoting the growth of keratinous fibres, in particular hair growth or regrowth, in particular for maintaining and/or increasing hair density in humans.

In human beings, the growth of hair and its renewal are mainly determined by the activity of the hair follicles and their cutaneous and/or connective environment. Their activity is cyclic and comprises essentially three phases, namely the anagen phase, the catagen phase and the telogen phase.

The active anagen phase or growth phase, which lasts for several years and during which the hair grows longer, is followed by a very short and transient catagen phase which lasts for a few weeks. During this phase, the hair undergoes an involution, the follicle is atrophied and its dermal implantation appears increasingly high.

The terminal phase, termed telogen phase, which lasts for a few months, corresponds to a resting period for the follicle and the hair finally falls out. After this resting phase, a new follicle is regenerated, in place, and another cycle begins.

The hair is therefore continuously renewed, and of the approximately 150 000 hair strands which make up the hair, at each instant, approximately 10% of them are in the resting phase and will therefore be replaced in a few months.

The natural loss of hair can be estimated, on average, at a few hundred hair strands per day for a normal physiological state. This process of permanent physical renewal undergoes a natural evolution during ageing, the hair becomes thinner, and its cycles shorter.

In addition, various causes can result in a transient or permanent loss of hair.

This may involve hair loss and damage towards the end of pregnancy (postpartum effluvium), during states of undernourishment or of dietary imbalances, or during states of asthenia or of hormonal dysfunction as may be the case during or towards the end of menopause. It may also involve hair loss or damage in relation to seasonal phenomena.

It may also involve alopecia which is essentially a disruption in hair renewal which causes, in the first instance, the acceleration of the frequency of the cycles at the expense of the quality of the hair and then of its quantity. Successive growth cycles result in increasingly thin and increasingly short hair, gradually changing to a nonpigmented down. Some areas are preferentially affected, in particular the temporal or frontal sinuses in men, and in women a diffuse alopecia of the vertex is observed.

The term alopecia also covers a whole family of impairments of the hair follicles of which the final consequence is the partial or general permanent loss of hair.

It involves more particularly androgenic alopecia. In a large number of cases, premature hair loss occurs in genetically predisposed subjects, it then involves androchronogenetic alopecia; this form of alopecia applies to men in particular.

It is moreover known that certain factors such as hormonal imbalance, physiological stress and malnutrition can intensify the phenomenon.

In certain dermatoses of the scalp with an inflammatory characteristic, such as for example psoriasis or seborrhoeic dermatitis, hair loss can be greatly intensified or can cause greatly disrupted hair cycles.

Compositions which make it possible to suppress or reduce alopecia, and in particular to induce or stimulate growth of hair or to reduce its loss, have been sought for many years in the cosmetics or pharmaceutical industry.

For this purpose, a large number of compositions comprising widely varying active agents have already been proposed, such as for example 2,4-diamino-6-piperidinopyrimidine 3-oxide or "Minoxidil" described in U.S. Pat. No. 4,139,619 and U.S. Pat. No. 4,596,812 or its many derivatives such as those described for example in patent applications EP 0353123, EP 0356271, EP 0408442, EP 0522964, EP 0420707, EP 0459890 and EP 0519819.

Clinical studies have demonstrated that PGF2α analogues had the property of causing the growth of body hair and of eyelashes in humans and in animals (Murray A and Johnstone M D, 1997. *Am J Opht,* 124(4), 544-547). In humans, trials carried out on the scalp have shown that a prostaglandin E2 analogue (viprostol) had the property of increasing hair density (Roenigk H H., 1988, *Clinic Dermatol,* 6(4), 119-121).

Patent WO 98/33497 describes pharmaceutical compositions containing prostaglandins or derivatives of prostaglandins intended for controlling hair loss in humans. Types A2, F2α and E2 prostaglandins are preferred.

However, prostaglandins are molecules which have a very short biological half-life period and which act in an autocrine or paracrine manner, reflecting a labile character due to a very active local metabolism of the prostaglandins (Narumiya S et al., 1999, *Physiol Rev,* 79(4), 1193-1226).

It therefore appears to be important, in order to maintain and/or increase hair density in humans, to preserve the endogenous reserves of PGF2α as well as of PGE2 of the different compartments of the hair follicle or of its close cutaneous environment.

A solution which gives good results is the administration of lipoxygenase inhibiting and/or cyclooxygenase inducing compounds so as to promote hair growth; a hypothesis is that the administration of such compounds orients the metabolism of fatty acids towards the endogenous synthesis of prostaglandins, rather than using other pathways.

However, to further improve the results, it would be desirable to be able to prolong the activity of the prostaglandins involved in the growth and the maintenance of the activity of the hair follicle.

It is moreover well known that the programmes of differentiation of the keratinocytes of the epidermis and of the hair follicle are clearly different. Thus it is known that the keratins of the hair shaft represent a family (Langbein et al., 2001, J. Biol. Chem. 276: 35123-35132) distinct from that expressed in the epidermis, that differentiation markers such as keratins K1 and K10 are not expressed in the hair follicle and in particular in the outer sheath (Lenoir et al., 1988, Dev.

Biol. 130: 610-620), that trichohyalin (O'Guin et al., 1992, J. Invest. Dermatol. 98: 24-32) and keratin K6irs (Porter et al., 2001, Br. J. Dermatol. 145: 558-568) are expressed in the hair follicle, in particular in the inner sheath but not in the epidermis, and that cyclooxygenase type 1, while being expressed in the epidermis, is not in the keratinocytes of the hair follicle but in the dermal papilla (Michelet. et al., 1997, J. Invest. Dermatol. 108:205-209).

Surprisingly, the applicant has now demonstrated that an enzyme which is specifically involved in the degradation of these prostaglandins is present in the dermal papilla of the hair, which is a critical compartment for the life of the hair. Indeed, the applicant has now proved the presence of 15-hydroxyprostaglandin dehydrogenase (15-PGDH) at this level. It has additionally shown that the specific inhibition of 15-PGDH has a beneficial effect on the hair density and/or growth.

Accordingly, the subject of the present invention is a composition, in particular a cosmetic composition, containing at least one 15-hydroxyprostaglandin dehydrogenase inhibitor and excipients which are physiologically acceptable, in particular from a cosmetic point of view.

The subject of the invention is thus the cosmetic use of at least one 15-PGDH inhibitor in or for the preparation of a composition intended for increasing the density of keratinous fibres and in particular hair, and/or reducing the heterogeneity of their diameter and/or promoting their growth.

The subject of the invention is also the cosmetic use of at least one 15-PGDH inhibitor in a care or make-up cosmetic composition for the eyelashes of human beings or for the preparation of a care and/or treatment composition for the eyelashes of human beings, for or intended for inducing and/or stimulating the growth of the eyelashes and/or increasing their density. This composition thus makes it possible to maintain the eyelashes in a good state and/or to improve their appearance.

Figure 1:
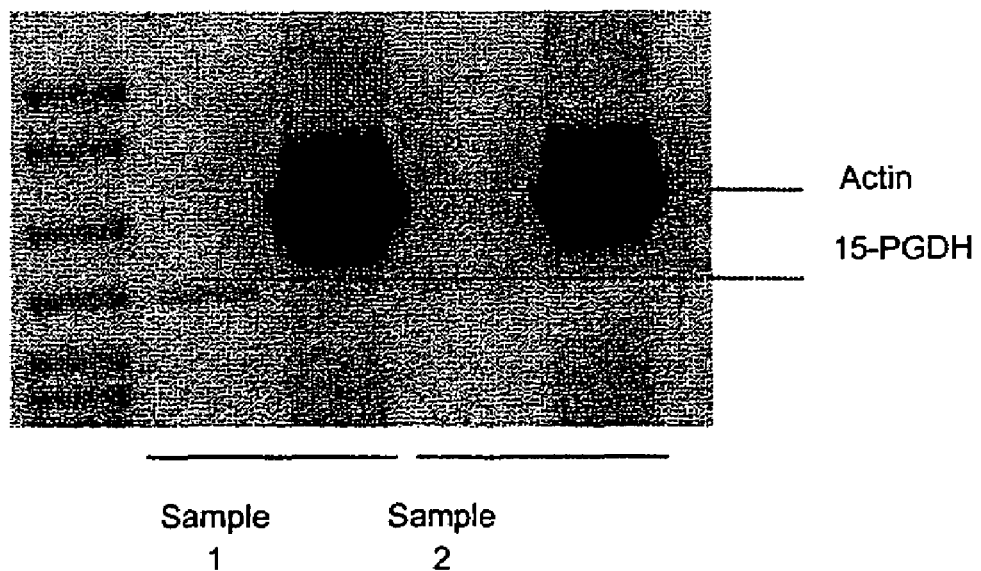
FIG. 1 illustrates the expression of 15-PGDH in the hair follicles from cultures of fibroblasts of dermal papillae of human hair in agarose gel under ultraviolet light; with a characteristic MW band shown at 706 bp.

15-PGDH is a key enzyme in the deactivation of prostaglandins, in particular of PGF2α, and of PGE2, which are important mediators of hair growth and survival. 15-PGDH type 1 corresponds to the EC 1.1.1.141 classification and is NAD+-dependent. It was isolated from pig kidney; its inhibition by a thyroid hormone, triiodothyronine, at doses which are much higher than physiological doses, has in particular been observed. 15-PGDH type 2 is NADP-dependent.

In the text which follows, the expression "15-PGDH" can denote either form of the enzyme, or both.

However, the presence of 15-PGDH in the dermal papilla has never been demonstrated, and it has never been proposed to use a 15-PGDH inhibitor for maintaining and/or increasing hair density and/or for reducing the heterogeneity of the hair diameters in humans.

The expression "15-PGDH inhibitor" is understood to mean, for the purposes of the invention, any substance, simple or complex compound, of natural or synthetic origin, capable of inhibiting or reducing the activity of the 15-PGDH enzyme, and/or capable of inhibiting, reducing or slowing the reaction catalysed by this enzyme.

Advantageously, the inhibitor is an inhibitor specific for 15-PGDH type 1.

The expression "heterogeneity of the hair diameters" is understood to mean a wide variation in the diameters of the hair in the same region of the scalp; some hair strands having a physiological diameter of close to 100 μm, others having, in the immediate vicinity of these hair strands, a reduced diameter (thin hair). Thus, the expression "reducing the heterogeneity of the diameters" is understood to mean increasing the diameter of thin hair.

The expression increasing the hair density is understood to mean increasing the number of hair strands per $cm^3$ of scalp.

Advantageously, a composition according to the invention will comprise excipients suitable for administration to the targeted skin area or keratinous fibre, and in particular the scalp, the hair or the eyelashes. The medium in which the 15-PGDH inhibitor is present according to the invention may be anhydrous or aqueous. The composition will comprise for example a cosmetologically acceptable medium which may consist of water or of at least one solvent chosen from hydrophilic organic solvents, lipophilic organic solvents, amphiphilic organic solvents and mixtures thereof, in particular a mixture of water and at least one of the above-mentioned solvents.

For topical application, the composition which can be used according to the invention may be in particular in the form of an aqueous, aqueous-alcoholic or oily solution or of a dispersion of the lotion or serum type, of emulsions of liquid or semiliquid consistency of the milk type, which are obtained by dispersing a fatty phase in an aqueous phase (O/W) or conversely (W/O) or multiple emulsions, of a loose or compact powder to be used as it is or to be incorporated into a physiologically acceptable medium, or of suspensions or emulsions of a soft consistency of the aqueous or anhydrous cream or gel type, or alternatively of microcapsules or microparticles, or of vesicular dispersions of the ionic and/or nonionic type. It may also be provided in the form of a salve, a tincture, a cream, an ointment, a powder, a patch, an impregnated pad, a solution, an emulsion or a vesicular dispersion, a lotion, a gel, a spray, a suspension, a shampoo, an aerosol or a foam. It may be anhydrous or aqueous. It may also consist of solid preparations constituting cleansing soaps or cakes.

These compositions are prepared according to the customary methods.

The composition which can be used according to the invention may in particular consist of a composition for hair care, and in particular a shampoo or an after-shampoo, in particular for twice-weekly or weekly application, a hair shaping lotion, a treatment lotion, a hair care lotion, for example for daily or twice-weekly application, a hair styling cream or gel, restructuring lotions for hair, a mask, and the like.

The cosmetic composition according to the invention will be preferably a cream, a hair lotion, a shampoo or an after-shampoo, hair mascara or mascara for the eyelashes.

For application to the eyelashes or body hair, the composition to which the invention applies may be provided in the form of a mascara, pigmented or otherwise, to be applied with a brush or with a comb to the eyelashes, the eyebrows, the hair, or to beard or moustache hair.

For a composition for use by injection, the composition may be provided in the form of an aqueous lotion or an oily suspension. For use orally, the composition may be provided in the form of capsules, granules, syrups to be taken orally or tablets.

The quantities of the various constituents of the compositions which can be used according to the invention are those conventionally used in the fields considered.

The aqueous phase contains water and optionally an ingredient which is miscible in any proportion with water such as $C_1$ to $C_8$ lower alcohols such as ethanol, isopropanol, polyols such as propylene glycol, glycerol, sorbitol, or acetone or ether.

When the composition which can be used according to the invention is an emulsion, the proportion of the fatty phase may range from 2 to 80%, in particular from 5% to 80% by weight, and preferably from 5% to 50% by weight relative to the total weight of the composition. The oils, waxes, emulsifiers and coemulsifiers used in the composition in the form of an emulsion are chosen from those conventionally used in the cosmetic field. The emulsifier and the coemulsifier are present in the composition in a proportion ranging from 0.1, in particular from 0.3% to 30% by weight, preferably from 0.5 to 20% by weight, and even better from 1 to 8% relative to the total weight of the composition. The emulsion may additionally contain lipid vesicles and in particular liposomes.

When the composition which can be used according to the invention is an oily solution or gel, the fatty phase may represent more than 90% of the total weight of the composition.

Advantageously, the composition will comprise microspheres, nanospheres, liposomes, oleosomes or nanocapsules, into which at least one 15-PGDH inhibiting agent will be encapsulated. Examples of such formulations are described in particular in patents EP 199636, EP 375520, EP 447318, EP 557489, WO 97/12602, EP 1151741 or U.S. Pat. No. 5,914,126.

By way of example, the microspheres may be prepared according to the method described in patent application EP 0 375 520.

The nanospheres may be provided in the form of an aqueous suspension and may be prepared according to the methods described in patent applications FR 0015686 and FR 0101438.

The oleosomes consist of an oil-in-water emulsion formed by oily globules provided with a lamellar liquid crystal coating dispersed in an aqueous phase (see patent applications EP 0 641 557 and EP 0 705 593).

The 15-PGDH inhibitor may also be encapsulated into nanocapsules consisting of a lamellar coating obtained from a silicone surfactant as described in patent application EP 0 780 115; the nanocapsules may also be prepared based on water-dispersible sulphonic polyesters for example according to the technique described in patent application FR 0113337.

Advantageously, for a hair application, the composition is an aqueous, alcoholic or aqueous-alcoholic solution or suspension, and even better a water/ethanol solution or suspension. The alcoholic fraction may represent from 5% to 99.9% and even better from 8% to 80%.

For a mascara application, the composition is a wax-in-water or wax-in-oil dispersion, a gelled oil, an aqueous gel, pigmented or otherwise.

In a known manner, the composition according to the invention may also contain adjuvants which are customary in the cosmetic field, such as hydrophilic or lipophilic gelling agents or thickeners, hydrophilic or lipophilic additives, preservatives, antioxidants, solvents, perfumes, fillers, screening agents, odour absorbers, electrolytes, neutralizers, UV blocking agents such as sun-screening agents, film-forming polymers, cosmetic and pharmaceutical active agents with a beneficial action on the skin or the keratinous fibres and dye substances, which are soluble or insoluble in the medium. The quantities of these various adjuvants are those conventionally used in the cosmetic field, and in particular are from 0.01 to 50% of the total weight of the composition, for example from 0.01% to 20%, in particular less than or equal to 10% of the total weight of the composition, and in particular greater than or equal to 0.1%. These adjuvants, depending on their nature, may be introduced into the fatty phase, into the aqueous phase and/or into the lipid spherules, vesicles or microspheres, such as liposomes.

The fatty phase may contain fatty or oily compounds, which are liquid at room temperature (25° C.) and atmospheric pressure (760 mmHg), generally called oils. These oils may be compatible or otherwise with each other and may form a macroscopically homogeneous liquid fatty phase or a two- or three-phase system.

The fatty phase may, in addition to the oils, contain waxes, gums, lipophilic polymers, "pasty" or viscous products containing solid parts and liquid parts.

As oils or waxes which can be used in the invention, there may be mentioned mineral oils (petroleum jelly, hydrogenated isoparaffin), vegetable oils (liquid fraction of shea butter, sunflower oil, soya-bean oil, wheat oil), animal oils (perhydrosqualene), synthetic oils (Purcellin oil, fatty acid esters), silicone oils or waxes (linear or cyclic polydimethylsiloxanes, cyclomethicone, phenyltrimethicone) and fluorinated oils (perfluoropolyethers), beeswax, candelilla wax, carnauba wax or paraffin wax. It is also possible to add fatty alcohols and free fatty acids (stearic, linoleic or linolenic acid) to these oils and waxes.

As emulsifiers which can be used in the invention, there may be mentioned for example glyceryl stearate or laurate, sorbitol stearates or oleates, alkyl dimethiconecopolyol (with alkyl$\geq$8) and mixtures thereof; polyoxyethylenated sorbitol stearate or oleate, for example polysorbate 60 and the PEG-6/PEG-32/glycol stearate mixture sold under the name Tefose® by the company Gattefosse, polyethylene glycol monostearate or monolaurate, dimethicone copolyols and mixtures thereof.

As solvents which can be used in the invention, there may be mentioned lower alcohols, in particular ethanol and isopropanol, and propylene glycol.

As hydrophilic gelling agents which can be used in the invention, there may be mentioned carboxyvinyl polymers (carbomer), acrylic copolymers such as acrylate/alkyl acrylate copolymers, polyacrylamides, polysaccharides such as hydroxypropylcellulose, natural gums and clays, and, as lipophilic gelling agents, there may be mentioned modified clays such as Bentones®, metal salts of fatty acids such as aluminium stearates and hydrophobic silica, ethyl cellulose, and polyethylene.

Preferably, the inhibiting agent(s) are present at a concentration greater than or equal to $10^{-3}$%, in particular of 0.001% to 5% w/v relative to the composition, more preferably of 0.01 to 2%. However, these quantities will be adjusted by persons skilled in the art according to the compound used, in order to obtain an optimum anti-hair-loss activity and an enzyme inhibition activity equivalent to a practically total inhibition of the 15-PGDH enzyme, under conditions for applying the composition, the concentration used being generally greater than or equal to that for which a 100% inhibition of 15-PGDH is observed in vitro. The concentration of 15-PGDH inhibiting agent will be in particular 50 to 500 times higher than the concentration for which 100% inhibition of 15-PGDH was observed in vitro, for example concentrations about 100 times that corresponding to a total inhibition in vitro will be used.

Suitable 15-PGDH inhibitors may be determined by persons skilled in the art; the inhibiting agent will be chosen in particular from traxanox, its salts and its esters.

According to a particularly advantageous embodiment of the invention, the composition will comprise at least one inhibitor specific for 15-PGDH; the expression "specific inhibitor" is understood to mean an active agent which is scarcely or not inhibitory for the synthesis of prostaglandins, in particular for the synthesis of PGF2α or of PGE2. Preferably, the 15-PGDH inhibitor will be scarcely or not inhibitory for prostaglandin synthase (PGF synthase).

Indeed, in the context of its research studies, the applicant has now found, unexpectedly, that PGF synthase is also expressed in the dermal papilla. Maintaining an effective quantity of prostaglandins at the site of action therefore results from a complex biological balance between the synthesis and the degradation of these molecules. The exogenous supply of compounds exhibiting catabolism will therefore be less effective if this activity is combined with an inhibition of synthesis.

As a supplement or as a replacement for this exogenous supply, the applicant has now demonstrated that it is possible to promote the maintenance of an endogenous prostaglandin pool, and therefore the maintenance or even the increase in the density of the keratinous fibres, in particular of the hair density, and the maintenance of the quality of the keratinous fibres, in particular of hair.

As an application of the present invention, it is now possible to target particularly active compounds, for which the 15-PGDH inhibiting activity is significantly greater than the PGF synthase inhibiting activity. The ratio between the respectively 15-PGDH and PGF synthase inhibiting activities for the administered dose, determined in particular by the concentrations inhibiting 50% of the enzyme activity, will be at least greater than 1, preferably at least 3:1, advantageously greater than or equal to 5:1. Agents which are particularly suitable for carrying out the invention have a ratio between the 15-PGDH and PGF synthase inhibiting activities greater than or equal to 10:1, in particular greater than or equal to 15, preferably greater than or equal to 25:1.

In this regard, compounds suitable for carrying out the invention are the compounds corresponding to the following formulae:

Molecule A: 5-amino-4,6-dichloro-2-phenylpyrimidine

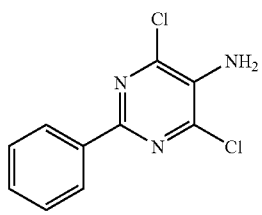

Molecule B: N-[7-(2-Chlorophenyl)-5-oxo-5,6,7,8-tetrahydroquinazolin-2-yl]benzamide

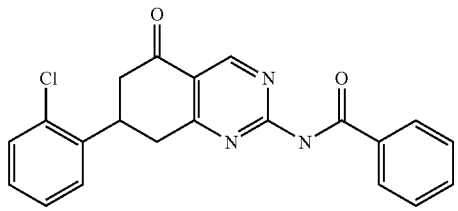

The choice of other agents which are active in the inhibition of 15-PGDH according to the present invention will be made by persons skilled in the art using a simple test starting with potential candidates. This test will consist in comparing the kinetics of a reaction catalysed by this enzyme, in a reaction medium comprising a substrate for the enzyme and possible cosubstrates, in the presence or otherwise of the compound whose 15-PGDH inhibiting role it is desired to evaluate; the reaction conditions (pH, temperature, reaction time, and the like) are those suitable for the reaction and are the same for the measurement in the presence or in the absence of the compound or substance to be tested.

For that, the following are for example brought into contact: the enzyme 15-PGDH at a final concentration of $7 \times 10^{-3}$ mg/ml, its cosubstrate (β-NAD) and a substrate (PGE2) at the concentrations corresponding to the conditions conventionally used for this test as described for example by Cho and Tai (Inhibition of NAD-dependent 15-hydroxyprostaglandin dehydrogenase (15-PGDH) by cyclooxygenase inhibitors and chemopreventive agents. Prostaglandins, Leukotrienes and Essential Fatty Acids, 2002, 67(6): 461-465), for example 1.5 mM β-NAD and 50 μM prostaglandin E2. The rate of the reaction is measured at 37° C. for 1 minute. The same reaction is carried out, but adding the test compound to the medium at the start of the reaction. The maximum enzyme reaction rate per unit of time (Vmax) measured in the presence of the compound is compared to that of the control with no compound, and the percentage inhibition [100−(Vmax assay×100)/Vmax control] is determined.

The compounds noted as 15-PGDH inhibitors are then tested for their capacity to inhibit PGF synthase. For that, the following are for example brought into contact: the enzyme PGFS at a final concentration of $25 \times 10^{-3}$ mg/l, its cosubstrate (β-NADPH2) and a substrate (for example phenanthrenequinone) at the concentrations conventionally used for this test as described for example by Suzuki et al. (cDNA cloning, expression and mutagenesis study of liver-type prostaglandin F synthase. *J Biol Chem*, 1999, 274(1): 241-248), that is to say 100 μM β-NADPH2 and 20 μM phenanthrenequinone. The maximum reaction rate is measured per unit of time at 37° C. The same reaction is carried out but adding the test compound to the medium at the start of the reaction. The maximum enzyme reaction rate with the compound is compared to that of the control with no compound, and the percentage inhibition [100−(Vmax assay×100)/Vmax control] is determined.

The percentage inhibition of the reaction catalysed by 15-PGDH and that of the reaction catalysed by PGFS is then compared. More precisely, the ratio of the IC50 values of a compound in relation to PGFS and 15-PGDH (IC50 PGFS/

IC50 15-PGDH) is established. The IC50 is the concentration of the compound for which Vmax is reduced by 50%.

The activity of compounds showing a selective inhibition of 15-PGDH for the purposes of the present invention may also be demonstrated by measuring the amount of prostaglandins in a cellular model mimicking the enzymatic environment of the hair papilla. This makes it possible to evaluate the efficacy of a selective 15-PGDH inhibitor on the protection of prostaglandins in a complex biological system producing the different types of enzyme involved in the metabolism of these molecules. For example, a culture of promonocytes is used, these being precursors of macrophages under certain conditions, a model which is very widespread for studying the metabolism of prostaglandins.

Indeed, the phorbol esters (10 nM PMA) cause within 24 h 00 min the differentiation of the promonocyte line U937 into macrophages; this differentiation is accompanied by the induction of 15-PGDH. (Tong and Tai, *Biochim Biophys Acta*, 2000; 1497: 61-68).

Moreover, stimulation of these macrophages by LPS (lipopolysaccharide extracted from the bacterial wall) induces (at 100 ng/ml) in 6 h 00 min PGHS-2 (or COX-2), an enzyme responsible (in the same way as COX-1) for the synthesis of PGH2, a precursor (inter alia) via PGFS, of PGF2α (Arias-Negrete et al., 1995. *Biochem Biophys Res Commun*, 208(2), 582-589).

In a 1st stage, macrophage precursors are cultured in a suitable medium, in the presence of a compound stimulating their differentiation and the induction of 15-PGDH, and then the production of prostaglandins by these cells is stimulated, for example by LPSs in the form of an extract or by purified LPSs; this 2nd stage is performed in the presence or otherwise of the compound to be tested. The concentrations of prostaglandins, in particular of PGF2α, obtained in the presence of the 15-PGDH inhibiting compound to be tested are compared to that of the control containing only the 15-PGDH inducer, it being possible to carry out this measurement by any method known to a person skilled in the art, in particular by immunoenzymatic assay. At the time of the assay, the quantity of PGF2α measured is therefore the resultant of the 2 enzymatic activities for which the compounds tested are more or less active: that of PGFS which leads to the synthesis of PGF2α and that of 15-PGDH which leads to the degradation. In the presence of a nonselective 15-PGDH inhibitor (also inhibitor of PGFS), a reduction in PGF2α will be observed (corresponding to a reduction in synthesis by the action of the product on PGFS). In the presence of an inhibitor selective for 15-PGDH, an increase in PGF2α will be observed, which corresponds to a reduction in degradation. The compounds for which the PGF2α level observed is greater by at least 5%, preferably by at least 10% than that of the control (inducer of the synthesis of prostaglandin alone) therefore have a prostaglandin F2α protecting role. Advantageously, for the compounds suitable for carrying out the invention, the prostaglandin concentration with the compound to be tested is equal to or greater by at least 20%, or even by 30% than that of the control.

Such compounds are in particular certain salified or nonsalified acetyltetrazoles, endowed with a surprising activity favourable to improving the hair density. The applicant has indeed found that these compounds are 15-hydroxyprostaglandin dehydrogenase inhibitors.

Another subject of the invention is therefore a hair care composition containing, in a physiologically acceptable medium, an effective quantity of a tetrazole compound of formula (I) or (II) or of one of its salts:

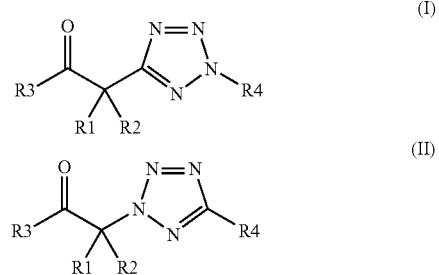

in which:

$R_1$ and $R_2$ are independently chosen from hydrogen, halogen, $OR_5$, $SR_5$, $NR_5R'_5$, $COOR_5$, $COR_5$, $CONR_5R'_5$, $CF_3$, $CN$, $NR_5COR'_5$, $SO_2R_5$, $SO_2NR_5R'_5$, $NR_5SO_2R'_5$, $CSR_5$, $OCOR_5$, $COSR_5$, $SCOR_5$, $CSNR_5R'_5$, $NR_5CONR'_5R''_5$, $NR_5C(=NR'_5)NR''_5R'''_5$, $NR_5CSR'_5$, $NR_5CSNR''_5R'''_5$, linear or branched $C_1$-$C_{20}$ alkyl radicals, and 4- to 7-atom rings, optionally containing at least one heteroatom, it being possible for these rings to be separated or fused, the alkyl radicals and the rings being additionally saturated or unsaturated, and optionally substituted with at least one substituent $A_1$, where $R_5$, $R'_5$, $R''_5$ and $R'''_5$ independently denote hydrogen, a linear or branched $C_1$-$C_{20}$ alkyl radical or a 4- to 7-atom hydrocarbon ring, the hydrocarbon ring or the alkyl radical being saturated or unsaturated and optionally substituted with at least one substituent $A_2$;

$R_3$ is chosen from hydrogen, $OR_6$, $SR_6$, $NR_6R'_6$, $CF_3$, $NR_6COR'_6$, $NR_6SO_2R'_6$, $NR_6CONR'_6R''_6$, $NR_6CSR'_6$, $NR_6CSNR'_6R''_6$, linear or branched $C_1$-$C_{20}$ alkyl radicals, and separated or fused 4- to 7-atom hydrocarbon rings, the alkyl radicals and the hydrocarbon rings being additionally saturated or unsaturated and optionally substituted with at least one substituent $A_3$, with $R_6$, $R'_6$ and $R''_6$ independently denoting hydrogen, a linear or branched $C_1$-$C_{20}$ alkyl radical, or a 4- to 7-atom hydrocarbon ring, the alkyl radical or the hydrocarbon ring being saturated or unsaturated and optionally substituted with at least one substituent $A_4$;

$R_4$ is chosen from hydrogen, $COOR_7$, $CONR_7R'_7$, $SO_2R_7$, $SO_2NR_7R'_7$, $COR_7$, $CSR_7$, $COSR_7$, $CSNR_7R'_7$, linear or branched $C_1$-$C_{20}$ alkyl radicals, and separated or fused 4- to 7-atom hydrocarbon rings, the alkyl radicals and hydrocarbon rings being additionally saturated or unsaturated and optionally substituted with at least one substituent $A_5$; $R_4$ may additionally represent, in the case of formula (II), a halogen, $OR_7$, $SR_7$, $NR_7R'_7$, $CF_3$, $CN$, $NR_7COR'_7$, $NR_7SO_2R'_7$, $OCOR_7$, $SCOR_7$, $NR_7CONR'_7R''_7$, $NR_7C(=NR'_7)NR''_7R'''_7$, $NR_7CSR'_7$ or $NR_7CSNR'_7R''_7$, with $R_7$, $R'_7$, $R''_7$ and $R'''_7$ independently denoting hydrogen, a linear or branched $C_1$-$C_{20}$ alkyl radical, or a 4- to 7-atom hydrocarbon ring, the alkyl radical or the hydrocarbon ring being saturated or unsaturated and optionally substituted with at least one substituent $A_6$;

$A_1$ and $A_2$ are independently chosen from halogens, heterocycles containing from 4 to 7 atoms and at least one heteroatom, $OR_8$, $SR_8$, $NR_8R'_8$, $COOR_8$, $CONR_8R'_8$, $CF_3$, $CN$, $NR_8COR'_8$, $SO_2R_8$, $SO_2NR_8R'_8$, $NR_8SO_2R'_8$, $COR_8$, $CSR_8$, $OCOR_8$, $COSR_8$, $SCOR_8$, $CSNR_8R'_8$, $NR_8CONR'_8R''_8$, $NR_8C(=NR'_8)NR''_8R'''_8$, $NR_8CSR'_8$, $NR_8CSNR'_8R''_8$;

$A_3$ and $A_4$ are independently chosen from halogens, $R_9$, $OR_9$, $SR_9$, $NR_9R'_9$, $COOR_9$, $CONR_9R'_9$, $CF_3$, $CN$, $NR_9COR'_9$, $SO_2R_9$, $SO_2NR_9R'_9$, $NR_9SO_2R'_9$, $CSR_9$, $OCOR_9$, $COSR_9$, $SCOR_9$, $CSNR_9R'_9$, $NR_9CONR'_9R''_9$, $NR_9C(=NR'_9)NR''_9R'''_9$, $NR_9CSR'_9$, $NR_9CSNR'_9R''_9$;

$A_5$ and $A_6$ are independently chosen from halogens, $R_{10}$, $OR_{10}$, $SR_{10}$, $NR_{10}R'_{10}$, $CF_3$, $CN$, $NR_{10}COR'_{10}$, $SO_2R_{10}$, $SO_2NR_{10}R'_{10}$, $NR_{10}SO_2R'_{10}$, $CSR_{10}$, $OCOR_{10}$, $SCOR_{10}$, $CSNR_{10}R'_{10}$, $NR_{10}CONR'_{10}R''_{10}$, $NR_{10}C(=NR'_{10})NR''_{10}R'''_{10}$, $NR_{10}CSR'_{10}$, $NR_{10}CSNR'_{10}R''_{10}$;

$R_8$, $R'_8$, $R''_8$, $R'''_8$, $R_9$, $R'_9$, $R''_9$, $R'''_9$, $R_{10}$, $R'_{10}$, $R''_{10}$ and $R'''_{10}$ independently denoting hydrogen, a saturated or unsaturated, linear or branched $C_1$-$C_{20}$ alkyl radical, a saturated or unsaturated 4- to 7-atom hydrocarbon ring, or a benzyl radical.

The invention also relates to the use of at least one tetrazole compound of formula (I) or (II) or tautomeric form or of one of its salts, as defined above, as agent for inducing and/or stimulating the growth of the hair of human beings and/or slowing its loss and/or increasing its density.

The invention also relates to the cosmetic use of at least one tetrazole compound of formula (I) or (II) or of one of its salts in a hair care cosmetic composition for human beings for reducing the loss of hair and/or increasing its density. Its subject is also the use of at least one tetrazole compound of formula (I) or of one of its salts for preparing a hair composition for human beings, intended for inducing and/or stimulating the growth of hair and/or slowing its loss and/or increasing its density.

In particular, the invention also relates to the cosmetic use of at least one tetrazole compound of formula (I) or (II) or of one of its salts in a hair care cosmetic composition for human beings or for preparing a hair composition for human beings intended for and/or for treating androgenic alopecia. Thus, this composition makes it possible to maintain the hair in a good state and/or to control the natural loss of hair in men.

The subject of the invention is also the use of at least one tetrazole compound of formula (I) or (II) or of one of its salts as a 15-hydroxyprostaglandin dehydrogenase inhibitor. Its subject is also the use of at least one tetrazole compound of formula (I) or (II) or of one of its salts for the manufacture of a composition intended for treating disorders linked to 15-hydroxyprostaglandin dehydrogenase in human beings.

Advantageously, the compounds of formula (I) or (II), in salified or nonsalified form, exhibit a 15-PGDH inhibiting activity which is greater than the PGF synthase inhibiting activity.

In the text which follows, and unless otherwise stated, the use of the term "compound of formula (I) or (II)" should be understood to mean both the compound of formula (I) or of formula (II) in acid or base form, and in salt form.

"At least one" according to the invention means one or more (2, 3 or more). In particular, the composition may contain one or more compounds of formula (I), one or more compounds of formula (II) or a mixture of compounds of formula (I) and of formula (II). This or these compounds may be cis or trans isomers or a mixture of cis/trans isomers. They may also be in tautomeric form. They may also be enantiomers and/or diastereoisomers or a mixture of these isomers, in particular a racemic mixture.

The expression "hydrocarbon" ring is understood, for the purposes of the invention, to mean a ring containing only carbon-carbon bonds to form the ring.

According to the invention, the rings used for $R_1$ to $R_4$ in the formulae (I) and (II) independently contain from 4 to 7 atoms and even better from 5 to 6 atoms. They may be saturated or unsaturated. They may furthermore be alone or fused with another ring of the same chemical structure or otherwise. In addition, $R_1$ and $R_2$ optionally contain one or more heteroatoms such as S, N, O or combinations thereof.

According to the invention, the rings used for $R_5$, $R'_5$, $R''_5$, $R'''_5$, $R_6$, $R'_6$, $R''_6$, $R'''_6$, $R_7$, $R'_7$, $R''_7$, $R'''_7$, $R_8$, $R'_8$, $R''_8$, $R'''_8$, $R_9$, $R'_9$, $R''_9$, $R'''_9$, $R_{10}$, $R'_{10}$, $R''_{10}$ and $R'''_{10}$ in the formulae (I) and (II) independently contain from 4 to 7 carbon atoms and even better from 5 to 6 carbon atoms. They may be saturated or even better unsaturated.

Moreover, the heterocycles used for $A_1$ and $A_2$ in the formulae (I) and (II) contain one or more heteroatoms such as S, N, O or combinations thereof. They additionally independently contain from 4 to 7 atoms and even better from 5 to 6 atoms. Furthermore, they may be saturated or unsaturated.

As saturated hydrocarbon rings which can be used in the formula (I) or (II), the cyclopentyl or cyclohexyl radical may be mentioned. As heterocycle, there may be mentioned the pyridine, piperidine, morpholine, pyrrole, furan and thiazole rings. As unsaturated hydrocarbon rings, the phenyl or naphthyl radical may be mentioned. In addition, these rings may be substituted with one or more substituents having the meaning indicated above for $A_1$, $A_2$, $A_3$, $A_4$, $A_5$ and $A_6$, depending on whether $R_1$, $R_2$, $R_3$, $R_4$, $R_5$, $R'_5$, $R''_5$, $R'''_5$, $R_6$, $R'_6$, $R''_6$, $R_7$, $R'_7$, $R''_7$ or $R'''_7$ is involved.

The expression "linear or branched $C_1$-$C_{20}$ alkyl radical" is understood to mean, according to the invention, the acyclic radicals obtained from the removal of a hydrogen atom from the molecule of a linear or branched hydrocarbon having from 1 to 20 carbon atoms, and in particular the methyl, ethyl, propyl, isopropyl, butyl, isobutyl, tert-butyl, pentyl, hexyl, heptyl and octyl radicals, and their corresponding position isomers. As example of (saturated) alkyl radical which can be used in the invention, there may be mentioned the methyl, ethyl, n-butyl, isopropyl and n-hexyl radicals.

As halogen atom, the chlorine, fluorine, iodine or bromine, and more especially chlorine, atoms may be used.

According to the invention, the compounds of formula (I) or (II) are in isolated, that is to say nonpolymeric, form. In addition, the substituents $A_1$, $A_2$, $A_3$, $A_4$, $A_5$ and $A_6$ may be situated at any position of the ring carrying them, and in particular at the position adjacent to the group carrying the tetrazole ring.

According to one embodiment, at least one of $R_1$ and $R_2$ represent a hydrogen atom, a halogen atom and in particular a fluorine or chlorine atom. In particular, $R_1$ and $R_2$ represent hydrogen.

Advantageously, $R_3$ represents $NR_6R'_6$ or an aryl radical, and in one particular embodiment a naphthyl or phenyl radical, optionally substituted with the substituent $A_3$. In particular, $A_3$ represents $OR_9$.

According to one embodiment, $R_6$ represents hydrogen and $R'_6$ an aryl, in particular a phenyl, radical optionally substituted with the group $OR_9$.

In particular, $R_9$ represents a saturated, linear or branched, $C_1$-$C_{20}$, and even better $C_1$-$C_{10}$, alkyl radical and for example the methyl radical.

According to one embodiment of the invention, $R_4$ represents an aryl radical and in particular a naphthyl or phenyl radical.

The expression "salts of the compound of formula (I) or (II)" is understood to mean, according to the invention, the organic or inorganic salts of a compound of formula (I) or (II).

As inorganic salts which can be used according to the invention, there may be mentioned the sodium or potassium salts, and the zinc ($Zn^{2+}$), calcium ($Ca^{2+}$), copper ($Cu^{2+}$), iron ($Fe^{2+}$), strontium ($Sr^{2+}$), magnesium ($Mg^{2+}$) and manganese ($Mn^{2+}$) salts; the hydroxides and the carbonates.

The organic salts which can be used according to the invention are for example the triethanolamine, monoethanolamine, diethanolamine, hexadecylamine, N,N,N',N'-tetrakis(2-hydroxypropyl)ethylenediamine and tris-hydroxymethylaminomethane salts.

Compounds suitable for carrying out the invention are in particular the 15-PGDH inhibiting compounds of formula (I) or (II) as defined above, in which:

$R_1$ and $R_2$ are independently chosen from hydrogen, halogens, $OR_5$, $SR_5$, $NR_5R'_5$, $COOR_5$, $CF_3$, CN, linear or branched $C_1$-$C_{20}$ alkyl radicals, and 4- to 7-atom rings, optionally containing at least one heteroatom, it being possible for these rings to be separated or fused, the alkyl radicals and the rings being additionally saturated or unsaturated, where $R_5$ and $R'_5$ independently denote hydrogen, a linear or branched $C_1$-$C_{20}$ alkyl radical, or a 4- to 7-atom hydrocarbon ring, the hydrocarbon ring or the alkyl radical being saturated or unsaturated;

$R_3$ is chosen from hydrogen, $OR_6$, $SR_6$, $NR_6R'_6$, $CF_3$, linear or branched $C_1$-$C_{20}$ alkyl radicals, and separated or fused 4- to 7-atom hydrocarbon rings, the alkyl radicals and the hydrocarbon rings being additionally saturated or unsaturated and optionally substituted with at least one substituent $A_3$, with $R_6$ and $R'_6$ independently denoting hydrogen, a linear or branched $C_1$-$C_{20}$ alkyl radical, or a 4- to 7-atom hydrocarbon ring, the alkyl radical or the hydrocarbon ring being saturated or unsaturated and optionally substituted with at least one substituent $A_4$;

$R_4$ is chosen from hydrogen, $COOR_7$, $CSR_7$, linear or branched $C_1$-$C_{20}$ alkyl radicals, and separated or fused 4- to 7-atom hydrocarbon rings, the alkyl radicals and the hydrocarbon rings being additionally saturated or unsaturated; $R_4$ may additionally represent, in the case of formula (II), a halogen, $OR_7$, $SR_7$, $NR_7R'_7$, $CF_3$, CN, with $R_7$ and $R'_7$ independently denoting hydrogen, a linear or branched $C_1$-$C_{20}$ alkyl radical, or a 4- to 7-atom hydrocarbon ring, the alkyl radical or the hydrocarbon ring being saturated or unsaturated, optionally substituted with at least one substituent chosen from $OR_{10}$, $SR_{10}$, $NR_{10}R'_{10}$, $CF_3$, with $R_{10}$ and $R'_{10}$ denoting a saturated or unsaturated, linear or branched $C_1$-$C_{20}$ alkyl radical;

$A_3$ and $A_4$ are independently chosen from halogens, $R_9$, $OR_9$, $SR_9$, $NR_9R'_9$, $COOR_9$, $CF_3$, with $R_9$ and $R'_9$ independently denoting hydrogen, a saturated or unsaturated, linear or branched $C_1$-$C_{20}$ alkyl radical, a saturated or unsaturated 4- to 7-atom hydrocarbon ring, or a benzyl radical.

According to another embodiment of the invention, the 15-PGDH inhibiting compounds are such that in formula (I) or (II) defined above, $R_3$ is chosen from hydrogen, $OR_6$, $SR_6$, $NR_6R'_6$, $CF_3$, linear or branched $C_1$-$C_{20}$ alkyl radicals, and separated or fused 4- to 7-atom hydrocarbon rings, the alkyl radicals and the hydrocarbon rings being additionally saturated or unsaturated and optionally substituted with at least one substituent $A_3$, with $R_6$ and $R'_6$ independently denoting hydrogen, a linear or branched $C_1$-$C_{20}$ alkyl radical, or a 4- to 7-atom hydrocarbon ring, the alkyl radical or the hydrocarbon ring being saturated or unsaturated and optionally substituted with at least one substituent $A_4$;

$R_4$ is chosen from hydrogen, linear or branched $C_1$-$C_{20}$ alkyl radicals, and separated or fused 4- to 7-atom hydrocarbon rings, the alkyl radicals and the hydrocarbon rings being additionally saturated or unsaturated, optionally substituted with at least one substituent chosen from $OR_{10}$, $SR_{10}$, $NR_{10}R'_{10}$, $CF_3$, with $R_{10}$ and $R'_{10}$ denoting a saturated or unsaturated, linear or branched $C_1$-$C_{20}$ alkyl radical;

$A_3$ and $A_4$ are independently chosen from $R_9$, $OR_9$, $SR_9$, $NR_9R'_9$, $COOR_9$, with $R_9$ and $R'_9$ independently denoting hydrogen, a saturated or unsaturated, linear or branched $C_1$-$C_{20}$ alkyl radical, a saturated or unsaturated 4- to 7-atom hydrocarbon ring, or a benzyl radical.

As examples of tetrazole compounds of formula (I) which can be used in the invention, the following compounds may be mentioned:

Compound 1: 1-phenyl-2-(2-phenyl-2H-tetrazol-5-yl)ethanone

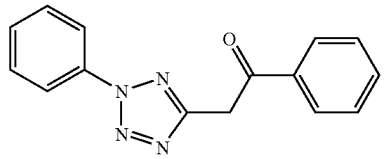

Compound 2: 1-(2-methoxyphenyl)-2-(2-phenyl-2H-tetrazol-5-yl)ethanone

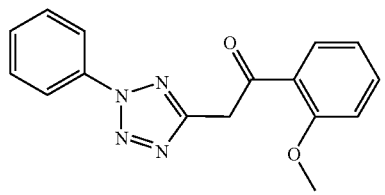

Ethyl 2-(2-phenyl-2H-tetrazol-5-yl)acetate

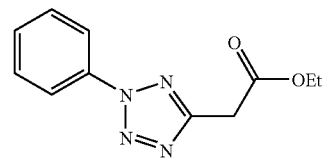

2-(2-phenyl-2H-tetrazol-5-yl)acetic Acid

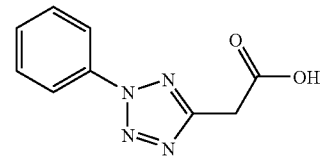

1-(3,4,5-trimethoxyphenyl)-2-(2-phenyl-2H-tetrazol-5-yl)ethanone

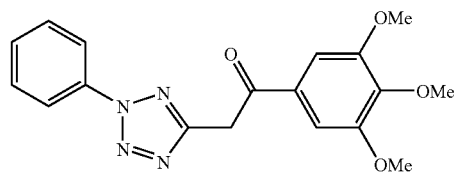

4-[2-(2-phenyl-2H-tetrazol-5-yl)acetyl]benzoic Acid

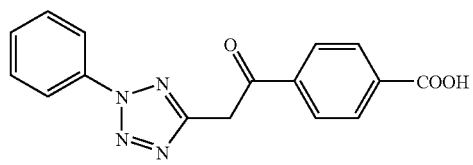

1-(4-benzyloxyphenyl)-2-(2-phenyl-2H-tetrazol-5-yl)ethanone

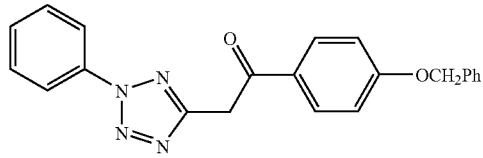

3-methoxy-1-phenyl-2-(2-phenyl-2H-tetrazol-5-yl)propan-1-one

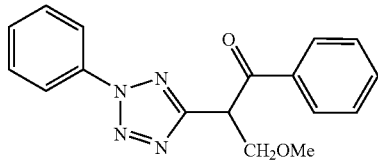

As examples of tetrazole compounds of formula (II) which can be used in the invention, the following compounds may be mentioned:

Compound 3: N-(2-phenyl)-2-(5-phenyl-2H-tetrazol-2-yl)acetamide

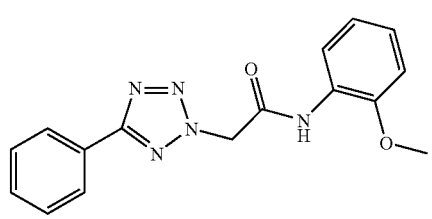

Compound 4: N-(2-methoxyphenyl)-2-(5-phenyl-2H-tetrazol-2-yl)acetamide

N-(4-methylphenyl)-2-{5-[3-(trifluoromethyl)phenyl]-2H-tetrazol-2-yl}acetamide:

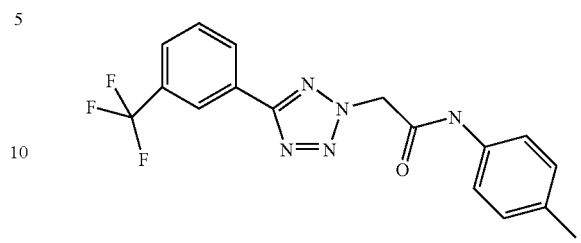

N-(2-methoxyphenyl)-2-(2H-tetrazol-2-yl)acetamide

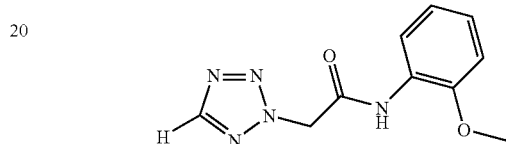

2-(5-phenyl-2H-tetrazol-2-yl)acetamide

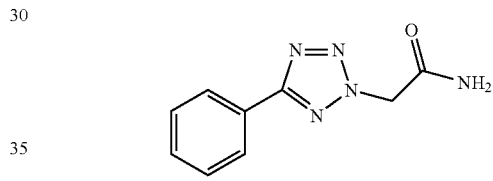

N-(2-methoxyphenyl)-2-[5-(2-naphthyl)-2H-tetrazol-2-yl]acetamide

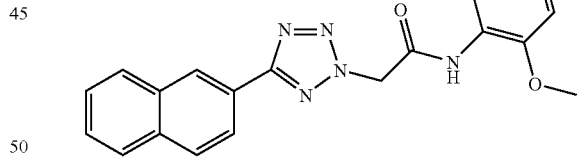

N-(2-methoxyphenyl)-2-[5-(4-methoxyphenyl)-2H-tetrazol-2-yl)acetamide

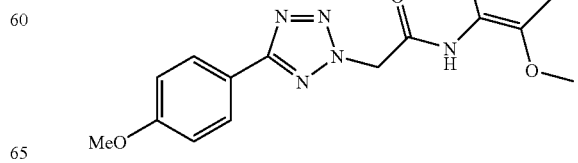

N-(3-hydroxypropyl)-2-(5-phenyl-2H-tetrazol-2-yl)acetamide

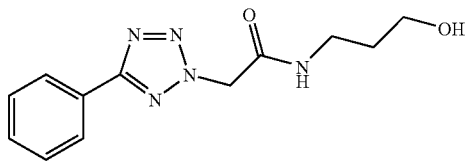

3-hydroxy-N-(2-methoxyphenyl)-2-(5-phenyltetrazol-2-yl)propionamide

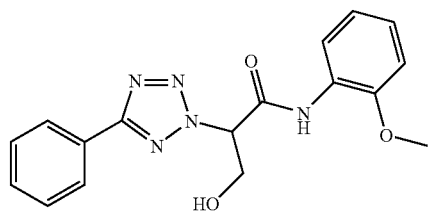

3-methoxy-N-(2-methoxyphenyl)-2-(5-phenyltetrazol-2-yl)propionamide

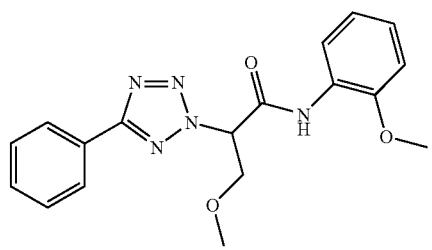

The compounds of formula (I) or (II), salified or otherwise, may be manufactured in a known manner.

1) Preparation of 5-acetyltetrazoles (Formula I)

The compounds of formula (I) of the invention may be prepared by a method described in the literature: D. Moderhack et al., J. Chem. Soc. Perkin Trans. 1, 2001, 720-728. The reaction scheme is the following:

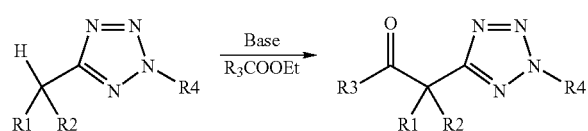

2) Preparation of 2-acetyltetrazoles (Formula II)

The compounds of formula (II) of the invention may be prepared by alkylation, with α-chlorocarbonyl-containing reagents, of tetrazoles substituted at the 5-position. This reaction is particularly suitable in the case of the synthesis of 5-phenyltetrazoles (corresponding to $R_4$=phenyl). This type of preparation is known to persons skilled in the art and in particular from the document F. Eindberg, J. Org. Chem., 1970, 35, 11, 3978-3980.

The reaction scheme may be the following:

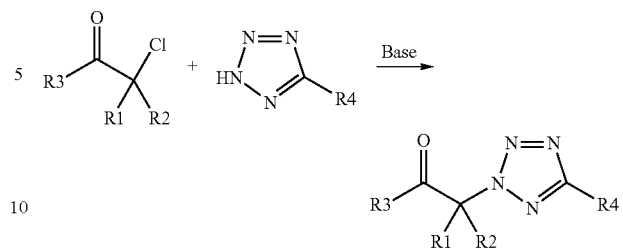

To the knowledge of the applicant, no prior art document describes or suggests that the tetrazole compounds of formula (I) or (II) or their salts have properties of inducing and/or stimulating the growth of hair and/or of slowing its loss or that these compounds may be used topically to increase hair density.

The effective quantity of a compound of formula (I) or (II) or of one of its salts corresponds to the quantity necessary to obtain the desired result (namely to increase the hair density). Persons skilled in the art are therefore able to evaluate this effective quantity which depends on the nature of the compound used, on the person to which it is applied, and on the time of this application.

In the text which follows, unless otherwise stated, the quantities of the various ingredients of the composition are given as the percentage by weight relative to the total weight of the composition.

To give an order of magnitude, according to the invention, the compound of formula (I) or one of its salts may be used in a quantity representing from $10^{-3}$% to 5% of the total weight of the composition, and preferably in a quantity representing from $10^{-2}$% to 2% of the total weight of the composition, for example from 0.5 to 2%.

The composition of the invention may be for cosmetic or pharmaceutical use. Preferably, the composition of the invention is for cosmetic use. Accordingly, the composition should contain a physiologically acceptable medium which is nontoxic and capable of being applied to the skin, the superficial body growths or the lips of human beings. The expression "cosmetic" is understood to mean, for the purposes of the invention, a composition having a pleasant appearance, odour and feel.

The compound of formula (I) or (II), salified or otherwise, may be used in a composition which has to be ingested, injected or applied to the skin (over any skin area to be treated).

According to the invention, the compound of formula (I) or (I) may be used orally in a quantity of 0.1 to 300 mg per day, for example of 5 to 10 mg/d.

A preferred composition of the invention is a composition for cosmetic use and in particular for topical application to the skin, and more especially to the scalp.

According to an advantageous embodiment, the compositions according to the invention additionally comprise at least one agent which is beneficial to the hair, such as in particular silicones, vegetable, animal, mineral or synthetic oils, waxes, ceramides, pseudoceramides, cationic polymers, sunscreens and vitamins.

The silicones which can be used in accordance with the invention are in particular polyorganosiloxanes which are insoluble in the composition and may be provided in the form of oils, waxes, resins or gums.

The organopolysiloxanes are defined in greater detail in the book by Walter NOLL "Chemistry and Technology of Silicones" (1968) Academie Press. They may be volatile or nonvolatile.

The 15-PGDH inhibiting agents will, according to one of the embodiments of the invention, be combined with other active compounds in order to promote the regrowth and/or limit the loss of hair.

These compounds will be chosen in particular from lipoxygenase inhibitors as described in EP 648488, the bradykinin inhibitors described in particular in EP 845700, prostaglandins and their derivatives, in particular those described in WO 98/33497, WO 95/11003, JP 97-100091, JP 96-134242, the agonists or antagonists of the receptors for prostaglandins, the nonprostanoic analogues of prostaglandins as described in EP 1175891 and EP 1175890, WO 01/74307, WO 01/74313, WO 01/74314, WO 01/74315 or WO 01/72268.

Agents promoting hair growth which may be present in the compositions according to the invention include vasodilators, antiandrogens, cyclosporins and their analogues, antimicrobials, anti-inflammatory agents with the exception of the inhibitors selective for prostaglandin H synthase 1 or COX-1, triterpenes, alone or as a mixture.

The vasodilators such as the potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide may thus be present in the composition.

The antiandrogens which can be used include in particular 5α-reductase inhibitors such as finasteride and the compounds described in U.S. Pat. No. 5,516,779, cyprosterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226.

The antimicrobial compounds may be chosen from selenium derivatives, ketoconazole, triclocarban, triclosan, zinc pyrithione, itraconazole, asiatic acid, hinokitiol, mipirocine, and the compounds described in EP 680745, clinycine hydrochloride, benzoyl or benzyl peroxide and minocycline.

The anti-inflammatory agents may be chosen from inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11):1465-1473).

Other active compounds for promoting the growth and/or limiting the loss of hair, which are present in the compositions may also be chosen from the group comprising aminexil and its derivatives, 6-O-[(9Z,12Z)octadec-9,12-dienoyl] hexapyranose, as described in FR 027293, FR 0212828, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium panthotenate, panthenol, resorcinol, protein kinase C inhibitors, prostaglandin H synthase 1 or COX-1 activators as described in FR 2732597, glycosidase inhibitors, glycosaminoglycanase inhibitors, pyroglutamic acid esters, hexosaccharidic or acylhexosaccharidic acids, substituted ethylenearyls, N-acylated amino acids, flavonoids, derivatives and analogues of ascomycin, histamine antagonists, triterpenes such as ursolic acid and the compounds described in U.S. Pat. No. 5,529,769, U.S. Pat. No. 5,468,888, U.S. Pat. No. 5,631,282, saponins, proteoglycanase inhibitors, agonists and antagonists of oestrogens, pseudopterins, cytokines and growth factor promotors, IL-1 or IL-6 inhibitors, IL-10 promoters, TNF inhibitors, vitamins, such as vitamin D, analogues of vitamin B12 and panthotenol, hydroxy acids, benzophenones, esterified fatty acids as described in FR 027293, FR 0212828 and hydantoin.

According to an advantageous embodiment of the invention, the 15-PGDH inhibiting agent will be combined with an active compound for promoting the growth and/or limiting the loss of hair, which is capable of being metabolized by this enzyme. Indeed, by virtue of the work by the applicant, it is now known that certain compounds conventionally used for promoting the growth and/or delaying or preventing the loss of hair have a lower activity because of the presence of 15-PGDH through reduction of the concentration and/or accelerated disappearance of the substances from the site of action. In accordance with the present invention, it is now possible to obtain compositions having an increased efficacy, by combining an active compound for promoting the growth and/or delaying or preventing the loss of hair, which is capable of being metabolized by 15-PGDH and a 15-PGDH inhibitor as defined above. A synergistic action of the active agents will thus be obtained for promoting the growth and/or delaying or preventing the loss of hair in these compositions.

The composition will additionally contain, for example, at least one compound chosen from prostaglandins, in particular prostaglandin PGE1, PGE2, their salts, their esters, their analogues and their derivatives, in particular those described in WO 98/33497, WO 95/11003, JP 97-100091, JP 96-134242, in particular agonists of the prostaglandin receptors. It may in particular contain at least one compound such as the agonists (in acid form or in the form of a precursor, in particular in ester form) of the prostaglandin F2 alpha receptor (FP-R) such as for example latanoprost, fluprostenol, cloprostenol, bimatoprost, unoprostone, the agonists (and their precursors, in particular the esters such as travoprost) of the prostaglandin E2 receptors (EP1-R, EP2-R, EP3-R, EP4-R) such as 17-phenyl PGE2, viprostol, butaprost, misoprostol, sulprostone, 16,16-dimethyl PGE2,11-deoxy PGE1,1-deoxy PGE1, the agonists and their precursors, in particular esters, of the prostacycline (IP) receptor such as cicaprost, iloprost, isocarbacycline, beraprost, the agonists and their precursors, in particular the esters, of the prostaglandin D2 receptor such as BW245C ((4S)-(3-[(3R,S)-3-cyclohexyl-3-isopropyl]-2,5-dioxo)-4-imidazolidineheptanoic acid), BW246C ((4R)-(3-[(3R,S)-3-cyclohexyl-3-isopropyl]-2,5-dioxo)-4-imidazolidineheptanoic acid), the agonists and their precursors, in particular the esters, of the receptor for the thromboxanes A2 (TP) such as I-BOP ([1S-[[1a,2a(Z), 3b(1E,3S),4a]]-7-[3-[3-hydroxy-4-[4-(iodophenoxy)-1-butenyl]-7-oxabicyclo[2.2.1]hept-2-yl]-5-heptenoic acid).

Advantageously, the composition according to the invention will comprise at least one 15-PGDH inhibitor as defined above and at least one prostaglandin or one prostaglandin derivative such as for example the prostaglandins of series 2 including in particular PGF2α and PGE2 in saline form or in the form of precursors, in particular of the esters (example isopropyl esters), their derivatives such as 16,16-dimethyl PGE2,17-phenyl PGE2 and 16,16-dimethyl PGF2α, 17-phenyl PGF2α, prostaglandins of series 1 such as 11-deoxyprostaglandin E1, 1-deoxyprostaglandin E1 in saline or ester form, their analogues, in particular latanoprost, travoprost, fluprostenol, unoprostone, bimatoprost, cloprostenol, viprostol, butaprost, misoprostol, their salts or their esters. Preferably, the composition contains at least one FP receptor agonist as described for example in WO 03/009820 or a prostanoic or nonprostanoic agonist of the EP2 and/or EP4 receptors in particular as described in EP 1175892.

The compositions according to the invention may also contain penetration accelerating agents. These compounds are known to persons skilled in the art and improve the passage of the agents to the site of action; they will be conventionally present in the compositions at concentrations greater than or equal to 0.01%, in particular of 0.1 to 20% and preferably of 0.1 to 5%. Compositions of this type which can be used are for example urea and the compounds mentioned in application WO 01/74313.

According to another of its subjects, the invention relates to a method of cosmetic treatment for promoting the growth and/or reducing, preventing or delaying the loss of hair, characterized in that the activity and/or the expression of 15-PGDH by the hair follicle is inhibited or reduced, comprising the administration of at least one 15-PGDH inhibitor. This method will be adapted in particular in order to maintain or increase the hair density and to reduce the heterogeneity of the hair diameter, in physiological cases where these parameters are disrupted, in a transient manner. The administration of the 15-PGDH inhibiting agent(s) will be carried out in particular in the form of a composition as defined above.

The administration of the 15-PGDH inhibitor or of the composition containing it in the method according to the invention will be carried out by any route, in particular orally. However, the method is preferably carried out by topical administration, in situ.

The 15-PGDH inhibitors used in the method according to the invention are as defined above; in particular, at least one specific 15-PGDH inhibitor, that is to say little or no PGFS inhibitor, will be used.

According to one of the variants of the method according to the invention, a prostaglandin and/or a prostaglandin derivative will be additionally administered, such as for example prostaglandins of series 2 including in particular PGF2α and PGE2 in saline or ester form (for example isopropyl esters), their derivatives such as 16,16-dimethyl PGE2, 17-phenyl PGE2, 16,16-dimethyl PGF2α, 17-phenyl PGF2α, prostaglandins of series 1 such as 11-deoxyprostaglandin E1, 1-deoxyprostaglandin E1 in saline or ester form, their analogues, in particular latanoprost, fluprostenol, unoprostone, bimatoprost, cloprostenol, viprostol, butaprost, misoprostol in saline or ester form, such as travoprost.

The 15-PGDH inhibiting agent(s) will be applied alone or in the form of a mixture, and optionally in combination with other active agents for promoting the growth and/or delaying or preventing the loss of hair, or penetration accelerants as defined above.

It is also possible, for example, to apply the composition containing an effective quantity of a 15-PGDH inhibiting compound, for example of formula (I) or (II), salified or otherwise, in the evening, to keep it in contact overnight and optionally to shampoo in the morning. These applications may be repeated daily for one or more months depending on the individual.

Thus, the subject of the present invention is also a method for the cosmetic treatment of hair and/or of the scalp, intended to stimulate the growth of hair in human beings and/or to slow its loss, characterized in that it consists in applying to the hair and/or the scalp a cosmetic composition comprising an effective quantity of at least one 15-PGDH inhibiting compound, for example of formula (I) or (II) or of one of its salts, in leaving it in contact with the hair and/or the scalp, and optionally in rinsing the hair and/or the scalp.

This method of treatment has the characteristics of a cosmetic method in so far as it makes it possible to improve the aesthetic quality of the hair by giving it greater vitality and an improved appearance. In addition, it can be used daily for several months.

Advantageously, in the method according to the invention, between 5 and 500 μl of a solution or composition as defined above, comprising between 0.001% and 5% of inhibitor, is administered.

According to yet another of its aspects, the subject of the invention is the use of at least one 15-PGDH inhibitor as defined above, for the preparation of a composition intended for reducing hair loss and/or promoting hair regrowth in a mammal, and in particular in humans. The said composition will additionally comprise physiologically acceptable excipients, suitable for administration by the topical or systemic route. The 15-PGDH inhibitors will be used in particular according to the invention for the preparation of a composition, in particular a pharmaceutical, dermatological or cosmetic composition, in combination with excipients known to persons skilled in the art. All the variants of the cosmetic compositions described in the preceding text can be adapted for the preparation of the said composition.

According to one of its embodiments, the compositions of the invention are intended for preventing, reducing or slowing hair loss, especially for the treatment of alopecia, in particular of androgenetic alopecia; androgenetic alopecia is distinct from autoimmune alopecia such as alopecia areata.

The following examples are intended to illustrate the invention without limiting in any manner the scope thereof.

In these examples, reference will be made to the following figures:

FIG. 1: expression of 15-hydroxyPGDH in the hair follicles

Figure 2:
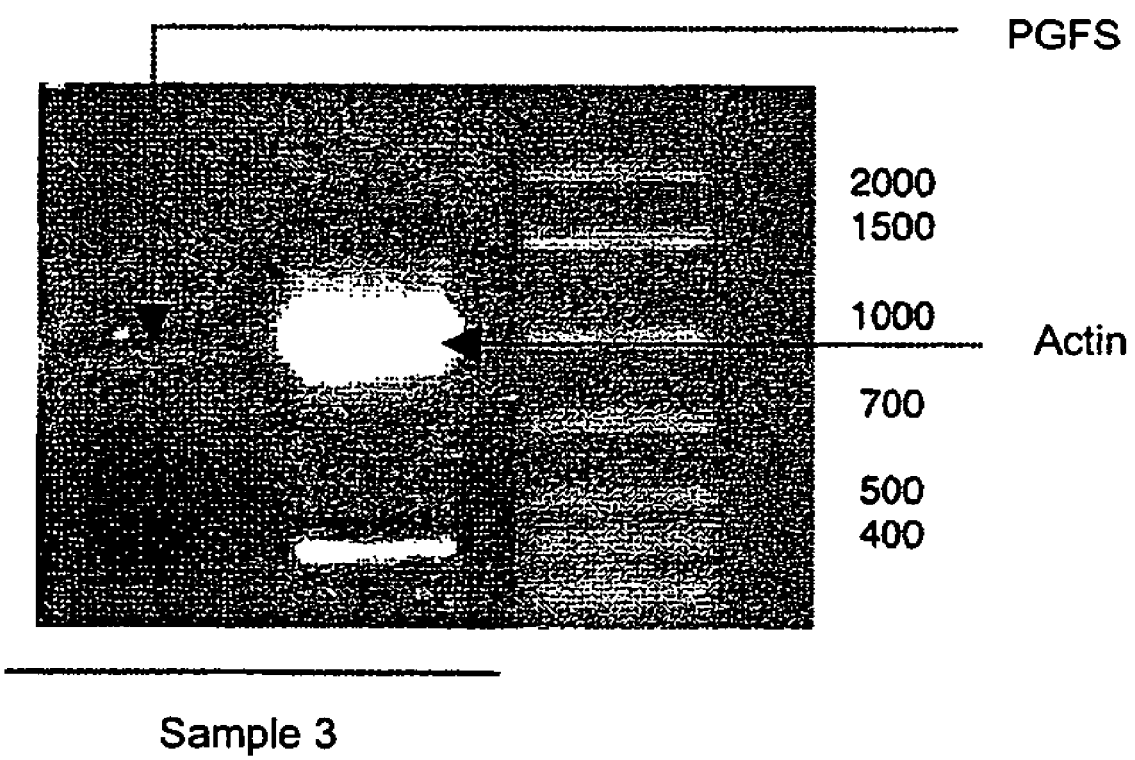
FIG. 2 illustrates the expression of prostaglandin synthase in the hair follicles from cultures of fibroblasts of dermal papillae of human hair in agarose gel under ultraviolet light, with a characteristic 1061 pb MW band shown.

FIG. 2: expression of prostaglandin synthase in the hair follicles

Figure 3:
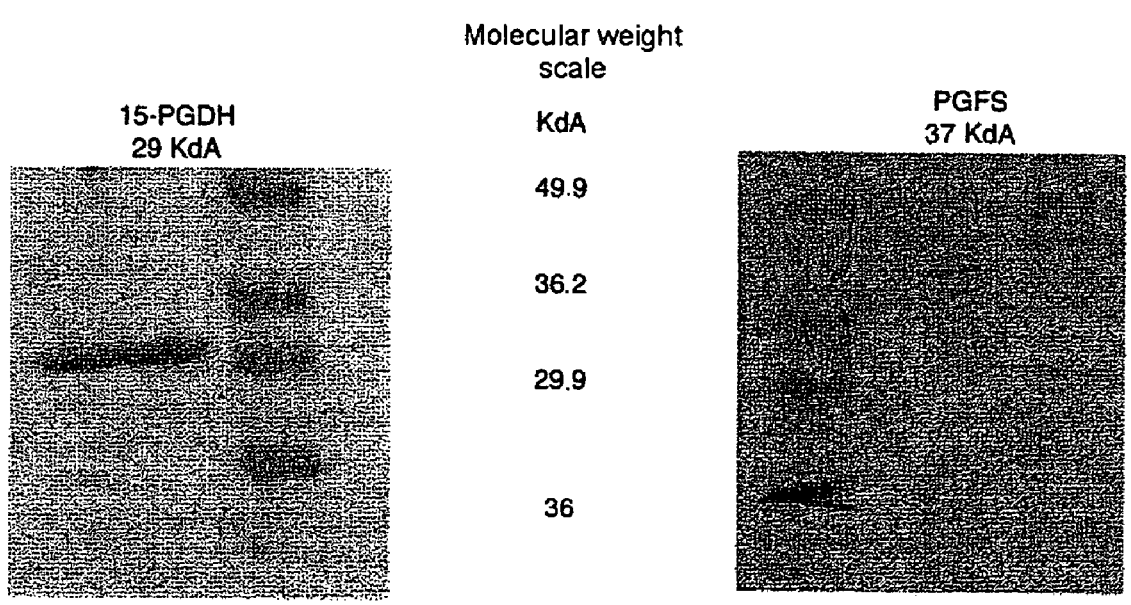
FIG. 3 depicts the results of electrophoretic analyses (SDS-page) of purified 15-PGDH and PGFS.

FIG. 3: electrophoretic analysis of purified 15-PGDH and PGFS

EXAMPLE 1

Demonstration of the Expression of the mRNA for 15-PGDH and PGFS in the Fibroblasts of Dermal Papillae of Hair in Culture 1. Dissection of the Hair Follicles Hair follicles obtained from lifting from volunteer donors are dissected according to the method described in the B. Bernard/O. Gaillard patent FR 2736721A1 of Jan. 17, 1997; U.S. Pat. No. 5,712,169A of Jan. 28, 1998.

The isolated follicles are placed in immersion in a Petri dish containing 20 ml of culture medium 199 Gibco reference 31153-018, Life Technologie, BP 96, Cergy Pontoise Cedex, supplemented with 1% (v/v) of an antibiotic solution Gibco reference 15240-096.

Using two needles, reference NN-2516R, Terumo Europe N. V., Leuven, Belgium, each mounted on a 1 ml syringe, reference BS-01N, Terumo, 15 dermal papillae are extracted from the follicular bulbs.

These 15 papillae are introduced into a Petri dish 35 mm in diameter, containing 2 ml of medium 199 previously used, containing 20% foetal calf serum Gibco, reference 10091-130. The dish is then placed in a thermostated incubator at 37° C. under 5% of $CO_2$.

A first passage is performed after 3 weeks of incubation without having replaced the medium beforehand. The medium is removed, 1 ml of trypsin solution Gibco reference 25050-022 is introduced into the Petri dish, the dish is again placed in the incubator for 4 minutes. The cells (fibroblasts of papillae) thus resuspended in trypsin solution (microscope check) are introduced into a 15 ml tube, reference Falcon, 352097, Becton Dickinson, Chemin des sources, BP 37, Meylan 38241, containing 10 ml of medium 199 previously used (containing 20% foetal calf serum).

After centrifuging for 5 minutes at 1 500 revolutions per minute, the supernatant is removed and the cell pellet is taken up in 5 ml of medium 199 previously used (containing here 10% foetal calf serum).

The cell suspension is introduced into a Petri dish 35 mm in diameter and placed again in the incubator (37° C., 5% $CO_2$).

The following passages P2, P3, P4 are performed according to the same principle. They are carried out when the cells have reached confluence.

2. Extraction and Purification of the Messenger RNAs

The extraction of the messenger RNAs from the fibroblasts of dermal papillae (performed on passages P3 or P4, 35 mm dish at confluence) is carried out according to the protocol and with the reagents of the QuickPrepr mRNA kit (Pharmacia Biotech, Brussels, Belgium). For each sample (a cell culture at confluence in a dish 35 mm in diameter) studied, the following protocol will be applied.

The cell culture supernatant is removed and replaced with 800 µl of lysis buffer, the lysate obtained is recovered and introduced into a 1.5 ml polypropylene microtube (tube 1).

1 ml of suspension of Oligo (dT-18) cellulose microspheres is introduced into a 1.5 ml microtube (tube 2) and centrifuged at 14 000 rpm for 1 minute. The supernatant is removed. The content of tube 1 is then introduced into tube 2, the microspheres are resuspended in the lysate by gently stirring the tube for 3 minutes.

The polyA+ RNAs attached to the microspheres are isolated from the contaminants by washing. The tube is centrifuged at 14 000 rpm for 1 minute, the supernatant is removed and replaced with 1 ml of washing buffer (high salt buffer). The microspheres are resuspended as above and the tube is gently stirred for 1 minute. The tube is centrifuged at 14 000 rpm for 1 minute, the supernatant is again removed and replaced with 1 ml of low salt buffer.

In total, five washes with the low salt buffer followed by three washes with the high salt buffer are thus carried out.

The content of the third wash (microspheres+buffer) is introduced into a microcolumn containing a filter at the base (microspin™ column) placed in a 1.5 ml microtube. The whole is centrifuged at 14 000 rpm for 1 minute. The microcolumn is recovered and placed in a 1.5 ml microtube. The polyA+ messenger RNAs are eluted with a total final volume of 0.4 ml of elution buffer previously heated to 65° C.

3. Precipitation of the Messenger RNAs

10 µl of glycogen solution, 40 µl of 2.5 M potassium acetate and 1 ml of absolute ethanol at −20° C. are introduced into the tube containing the eluate. The tube is placed in dry ice (−80° C.). After 1 h 00 min, the tube is centrifuged at 4° C. at 17 500 rpm for 15 minutes. The supernatant is carefully removed (the mRNAs form a very small pellet) and replaced with 1 ml of 80% ethanol (ethanol/water; v/v) at −20° C. The tube is centrifuged for 15 min at 17 500 rpm at 4° C. and the supernatant completely removed. The pellet is taken up in 8 µl of sterile distilled water.

4. Synthesis of Complementary DNA (cDNA) Strands

This step is performed using the First strand cDNA synthesis kit (Pharmacia Biotech, Brussels, Belgium).

The tube containing the mRNAs are placed at 65° C. for 10 minutes and then on ice for 5 minutes, and there are then introduced:

5 µl of a buffered solution containing a reverse transcriptase suspension,

1 µl of Oligo (dT-18) primers at 0.8 µg/ml,

1 µl of aqueous dithiothreitol solution having a titre of 200 nM.

The tube is incubated at 37° C. for 1 h 00 min. The reaction is blocked by placing the tube on ice.

5. Choice of the Primers, Polymerase Chain Reaction (PCR)

1 µl (of a 1/10 dilution in sterile distilled water) of complementary DNAs thus obtained is subjected, in a buffered medium, to a polymerase chain reaction (PCR), in the presence of specific pairs of primers (having a titre of 40 ng/ml), TAQ Polymerase and nucleotides according to the data from the supplier.

The primers specific for the sequences of interest which will be used are obtained by synthesis to order by Genset S A, rue Robert et Sonia Delaunay, Paris. The first pair of primers hybridized with the sequence encoding an ubiquitous protein (β-actin). The second pair of primers hybridized with the sequence encoding 15-hydroxyprostaglandin dehydrogenase.

Human β-actin; Genbank Accession No.: NM_001101
Sense primer (SEQ ID NO.:1): 5'-ATGGATGAT-GATATCGCCGCGCT-3'
Anti-sense primer (SEQ ID NO.:2): 5'-CGGACTCGTCAT-ACTCCTGCTTG-3'
Amplified fragment: 1 096 base pairs.

Human 15-hydroxyprostaglandin (15-PGDH); Genbank Accession No.: NM_000860
Sense primer (SEQ ID NO.:3): 5'-TGCCAATGGAT-TGATAACACTCAT-3'
Anti-sense primer (SEQ ID NO.:4): 5'-ACAG-CAGTTTTCATCTGGGATATG-3'
Amplified fragment: 706 base pairs.

Prostaglandin F Synthase (PGFS); Genbank Accession No.: AB018580
Sense primer (SEQ ID NO.:5): 5'-AATTCCGGGCAG-CAAACAT-3'
Anti-sense primer (SEQ ID NO.:6): 5'-ACACACAGGGCT-TCTGGTAGACA-3'
Amplified fragment: 1 061 base pairs.

The PCR reaction is carried out according to an adaptation of the TAKARA Taq™ protocol, TAKARA Shuzo Co. Ltd., Biomedical Group, Seta 3-4-1, Otsu, Shiga, 520-2193, Japan. The hybridization temperature is 54° C. for the pairs of primers (β-actin; PGFS, 15-PGDH), number of cycles=35.

The following are introduced into a microtube suitable for PCR:

1 µl (a 1/10 dilution) of complementary DNA,

43 µl of the mixture of nucleotides in buffered solution*,

*A buffered nucleotide solution is prepared by mixing 171 µl of sterile distilled water, 24.5 ml of 10× buffer from the kit and 20 µl of nucleotide (dNTP) mixture from the kit.

5 µl (2.5 µl+2.5 µl) of pairs of primers at 40 ng/µl are in reaction,

50 µl of mineral oil.

The tube is placed in a PCR apparatus and the following cycles are programmed:

| | |
|---|---|
| 4' at 95° C. | 1 cycle |
| 30" at 94° C. | |
| 1' at 54° C. | 35 cycles |
| 1' at 72° C. | |
| 7' at 72° C. | 1 cycle |

6. Reading 6.1 Preparation of an Agarose Gel

Weighing of 0.65 g of agar (Molecular biology certified agarose, Bio-Rad laboratories 2000 Alfred Nobel Dr., Hercules, Calif. 94547, USA).

Addition of 50 ml of 1×TAE buffer, Amresco, Solon, Ohio 44139, USA.

The agarose in suspension is heated to boiling temperature and then introduced into a tank containing a drop of ethydium bromide (25 µg), Amresco, Solon, Ohio 44139, USA.

A "comb" allowing the deposition of samples is placed at one end of the tank. After cooling for 30 minutes (room temperature), 20 µl of the PCR results are individually introduced into a well of the gel, as well as 10 µl of a mixture of molecular weight standards (Amplisize™, molecular Ruler, 170-8200, Bio-Rad laboratories 2000 Alfred Nobel Dr., Hercules, Calif. 94547, USA).

The whole is subjected, immersed in a large excess of 1×TAE buffer, to an electrical field of 100 volts for 45 minutes.

Exposure of the gel under ultraviolet light makes it possible to observe the results obtained by fluorescence.

Weight of the amplimers expected.

Actin 1 096 base pairs; 15-PGDH=707 base pairs; PGFS=1 061 base pairs.

Samples 1, 2, 3 are obtained from different cultures of fibroblasts of dermal papillae of human hair.

Test for the Expression of 15-hydroxyprostaglandin Dehydrogenase

The results are presented in FIG. 1.

It is observed that 15-PGDH is expressed in the different samples, with a characteristic MW band at 706 bp.

Test for the Expression of Prostaglandin F Synthase

The results are presented in FIG. 2.

It is observed that PGFS is expressed in the different samples, with a characteristic 1 061 pb MW band.

EXAMPLE 2

Cloning from Fibroblasts of Dermal Papillae of Hair and then Purification of PGFS and 15-PGDH The extraction and the purification of the poly-A+ messenger RNAs and then the synthesis of complementary DNA (cDNA) were carried out using a culture of fibroblasts of dermal papillae of hair as described in Example 1.

Pairs of primers (synthesized by Genset) to which were added sequences encoding restriction sites were chosen for 15-PGDH (Genbank accession No. NM_000860) and for PGFS (Genbank accession No.=AB018580).

a) Primers for 15-PGDH (SEQ ID NOS.:7 & 8)

5'-GGG GAT CCA TGC ACG TGA ACG GCA AAG TG-3'; sense primer BamH1 site (in bold)

5'-TCT CGA GAG CTG TTC ATT GGG T-3'; anti-sense primer Xho1 site (in bold)

b) Primers for PGFS (SEQ ID NOS.:9 & 10)

5'-CGG GAT CCA TGG ATT CCA AAC AGC AGT GTG-3'; sense primer BamH1 site (in bold)

5'-CG GAA TTC TTA ATA TTC ATC TGA A-3'; anti-sense primer EcoR1 site (in bold)

c) Polymerase chain reaction (PCR)

The PCR protocol applied for the cloning of 15-PGDH and for the cloning of PGFS is broadly similar to that described above, except for the differences below:

The Taq Polymerase used according to the manufacturer's data (Pfu Turbo$^r$ DNA Polymerase), Stratagene cloning systems, 11011 North Torrey Pines Road, La Jolla, Calif. 92037.

Hybridization temperature 59° C., extension time 2 min, 25 cycles in total for 15-PGDH, expected amplimer=815 bp.

Hybridization temperature 50° C., extension time 2 min, 25 cycles in total for PGFS, expected amplimer 989 bp.

d) The PCR products are digested with the restriction enzymes (BamH1; Xho1 for 15-PGDH and BamH1; EcoR1 for PGFS) according to the manufacturer's data (Amersham Pharmacia Biotech, 12 avenue des Tropiques, Z A Courtaboeuf, 91944 Les Ulis) and then individually run on a 1.3% agarose gel (see Example 1; 6. Reading).

e) Cutting out the bands corresponding to the expected amplimers (see ac) using a scalpel (after locating under ultraviolet light) and purification of these cut-outs according to the recommendations of the manufacturer of the Wizard$^r$ PCR Preps DNA Purification system kit (Promega Corporation, 2800 Woods Hollow Road, Madison, Wis. 53711-5399).

f) 15-PGDH

Ligation into a vector pGEX 4T3 (Amersham Pharmacia Biotech, 12 avenue des Tropiques, Z A Courtaboeuf, 91944 Les Ulis) previously digested (BamH1/Xho1) and purified, according to the information from the manufacturer of the Fast-Link™ DNA ligation kit, Epicentre, 1202 Ann Street, Wis. 53713.

PGFS

Ligation into a vector pGEX 2T (Amersham Pharmacia Biotech, 12 avenue des Tropiques, Z A Courtaboeuf, 91944 Les Ulis) previously digested (BamH1/EcoR1) and purified, according to the information from the manufacturer of the Fast-Link™ DNA Ligation kit, Epicentre, 1202 Ann Street, Wis. 53713. These two vectors allow the synthesis of the protein of interest coupled to a fusion protein (glutathione sulphotransferase). The fusion protein will allow subsequent purification of the protein of interest.

g) Transformations

Competent bacteria of the BL21DE3plys type will be used for the transformation with the construct (pGEX4T3/15-PGDH), competent bacteria of the BL21DE3 type for the transformation with the construct (PGEX 2T/PGFS). These two strains are marketed by the company Stratagene. The transformations are carried out according to a protocol which is conventionally applied as described for example in the Fast-Link™ DNA ligation kit previously used. The infected bacteria (clones) are selected (white colonies) after deposition and culture for 24 h 00 min. at 37° C. of a fraction of these transformation products on LB-Agar medium poured into a Petri dish (L-2897, Sigma-Aldrich, L'isle D'Abeau Chesne, BP 701, 38297, Saint Quentin Fallavier) containing 100 µg/ml of ampicillin.

h) Production of 15-PGDH and PGFS.

A colony obtained from the "15-PGDH transformation" Petri dish is collected and introduced into 250 ml of LB medium (L-3022, Sigma-Aldrich, L'isle D'Abeau Chesne, BP 701, 38297, Saint Quentin Fallavier) containing 100 µg/ml of ampicillin, the flask being incubated with stirring for 16 h 00 min at 37° C.

The same procedure is carried out in another flask, for a colony obtained from the "PGFS transformation" Petri dish.

After 16 h 00 min, each of the flasks is introduced into an Erlenmeyer flask containing 2.5 l of LB medium containing 100 µg/ml of ampicillin. These two Erlenmeyer flasks are incubated, with stirring, at 37° C. for 3 h 00 min to 4 h 00 min until the optical density, measured at 630 nm, is between 0.6-0.9).

Addition of isopropyl β-D-thiogalactopyranoside (IPTG), (16758, Sigma-Aldrich, L'isle D'Abeau Chesne, BP 701, 38297, Saint Quentin Fallavier) such that the final concentration is 0.1 mM.

The Erlenmeyer flasks are incubated for an additional 24 h 00 min, with stirring, at room temperature (20-25° C.). The cultures thus obtained are centrifuged (in 250 ml fractions) at 5 000 rpm for 7 minutes, the pellets are taken up in 3 ml of 10 mM phosphate buffer pH=7.00 (4° C.) containing a mixture of protease inhibitors (protease inhibitor cocktail set 1539131, Calbiochem-Novabiochem Corporation, 10394 Pacific Center Court, San Diego, Calif. 92121). The bacterial suspensions (grouped together into fractions of 40 ml in a polypropylene tube) are blocked on ice and subjected to ultrasound (Vibra cell 20 kHz, 72434, Bioblock scientific, Parc d'innovation, BP111, 67403 Illkirch) the probe being dipped into each tube for 15 seconds (6 shocks of 15 seconds per tube). Each tube is centrifuged at 4° C., 16 000 rpm, for 1 h 00 min.

i) Purification of 15-PGDH and PGFS

The supernatants are recovered and introduced into a polypropylene tube containing 1 ml of Glutathione-Sepharose$_r$ 4B (40 ml of supernatant per 1 ml of Glutathione-Sepharose$^r$ 4B) previously washed according to the recommendations of the manufacturer (Amersham Pharmacia Biotech, 12 avenue des Tropiques, Z A Courtaboeuf, 91944 Les Ulis).

The tubes are placed vertically on a rotary shaker, rotation 10 revolutions per minute for 1 h 00 min at room temperature (20-25° C.).

The tubes are centrifuged at 1 000 rpm for 3 minutes, and the supernatant is removed, the 40 ml of a 10 mM phosphate buffer pH=7.00 are introduced into each of the tubes. After gentle stirring (inverting) the tubes are again centrifuged for 3 minutes at 1 000 rpm.

The operation is performed 5 times. A sixth wash is performed with 40 ml of phosphate buffered saline pH=7.2 (PBS, Bio-Merieux S, 69280 Marcy-l'Etoile). After centrifugation, the supernatant is again removed.

j) Elution of 15-PGDH and PGFS

A suspension of thrombin protease is reconstituted at 1 unit/µl in PBS according to the recommendations of the manufacturer (Amersham Pharmacia Biotech, 12 avenue des Tropiques, Z A Courtaboeuf, 91944 Les Ulis).

950 µl of PBS and 50 µl of reconstituted thrombin suspension are introduced into each tube containing 1 ml of Glutathione-Sepharose$^r$ 4B. They are stirred in a slightly inclined position, 16 h 00 min at 250 rpm. After 16 h 00 min, the tubes are centrifuged at 3 000 rpm for 5 min and the supernatants are recovered. The quantity of protein is evaluated according to the Bio-Rad DC Protein Assay procedure (Bio-Rad Laboratories, 2000 Alfred Nobel Dr, Hercules, Calif. 94547).

Thus, for 15-PGDH as well as for PGFS, between 0.2 and 5 mg of protein are obtained per ml, most often 1 mg/ml.

The protein suspensions thus obtained are diluted respectively in PBS supplemented with 10% glycerol and PBS such that the final protein concentrations are 0.2 mg/ml for 15-PGDH and 0.5 mg/ml for PGFS. The suspensions are blocked at −80° C. until used.

Electrophoretic analyses (SDS-Page) performed under standard conditions demonstrate the quality of the results thus obtained. These results are presented in FIG. 3.

EXAMPLE 3

Evaluation of the Effect of Molecules on these Enzymes and Characterization of Certain Families of Molecules as Specific 15-PGDH Inhibitors a) 15-PGDH Test The enzyme obtained is at the concentration of 0.3 mg/ml and is blocked at −80° C. This suspension is thawed and stored on ice.

Preparation of a 100 mM Tris buffer pH=7.4 containing 0.1 mM dithiothreitol (D5545, Sigma-Aldrich, L'isle D'Abeau Chesne, BP 701, 38297, Saint Quentin Fallavier), 1.5 mM β-NAD (N6522, Sigma-Aldrich, L'isle D'Abeau Chesne, BP 701, 38297, Saint Quentin Fallavier), 50 µM Prostaglandin $E_2$ (P4172, Sigma-Aldrich, L'isle D'Abeau Chesne, BP 701, 38297, Saint Quentin Fallavier).

0.965 ml of this buffer (previously heated to 37° C.) is introduced into a spectrophotometer cuvette (Perkin-Elmer, Lambda 2) thermostated at 37° C., whose wavelength for measurement is set at 340 nm. 0.035 ml of enzymatic suspension at 37° C. are introduced into the cuvette concomitantly with the recording (increase in the optical density at 340 nm).

The maximum reaction rate is recorded.

The test values (molecules) are compared with the control value (with no molecule), the results are expressed as % of the control value.

b) PGFS Test

The enzyme obtained is at a concentration of 0.5 mg/ml and blocked at −80° C. This suspension is thawed and stored on ice.

Preparation in a brown flask (protection from light) of a 100 mM Tris buffer pH=6.5 containing 20 µM 9,10-phenanthrenequinone* (P2896, Sigma-Aldrich, L'isle D'Abeau Chesne, BP 701, 38297, Saint Quentin Fallavier) and 100 µM β-NADPH (N1630, Sigma-Aldrich, L'isle D'Abeau Chesne, BP 701, 38297, Saint Quentin Fallavier).

A stock solution having a titre of 1 mM is prepared in absolute ethanol heated to 40° C., the flask is placed in an ultrasonic tank in order to facilitate the solubilization of the product.

0.950 ml of this buffer (previously heated to 37° C.) is introduced into the cuvette of a spectrophotometer (Perkin-Elmer, Lambda 2) thermostated at 37° C. whose wavelength for measurement is set at 340 nm. 0.05 ml of enzymatic suspension at 37° C. is introduced into the cuvette concomitantly with the recording (reduction in the optical density at 340 nm).

The maximum reaction rate is recorded.

The test values (molecules) are compared with the control value (with no molecule), the results are expressed as % of the control value.

The results obtained for the molecules A and B are the following:

| at 50 μM | % Inhibition 15-PGDH | % Inhibition PGFS |
|---|---|---|
| Molecule A: 5-amino-4,6-dichloro-2-phenylpyrimidine | 43 | 5 |
| Molecule B: N-[7-(2-chlorophenyl)-5-oxo-5,6,7,8-tetrahydroquinazolin-2-yl]benzamide | 57 | 10 |

EXAMPLE 4

Demonstration of the Inhibitory Activity of the Compounds of Formula (I) or (II)

The test values (containing the compounds (I) or (II)) are compared with the control value (with no compound (I) or (II)) according to the protocol described in Example 3; the results indicated represent the % inhibition for a given concentration of the compound (I) or (II).

| Compound | Structure | Inhibition of 15-PGDH at 50 μM |
|---|---|---|
| 1 | 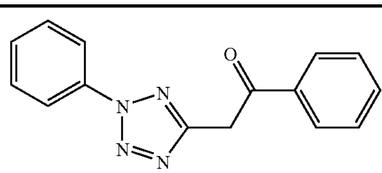 | 70% inhibition |
| 4 | 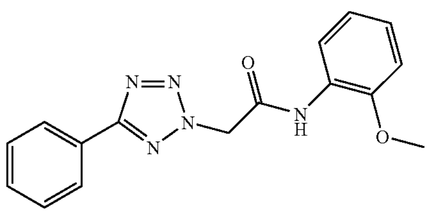 | 60% inhibition |

It is evident from this table that the compounds 1 and 4 are indeed 15-PGDH inhibitors. They will therefore allow a reduction in hair loss, in particular which is natural.

EXAMPLE 5

Characterization of Inhibitors Specific for 15-PGDH

The following compounds are tested according to the protocol of Example 3:

N-(2-Methoxyphenyl)-2-[5-phenyl-2H-tetrazol-2-yl]acetamide (compound 4)

1-Phenyl-2-(2-phenyl-2H-tetrazol-5-yl)ethanone (compound 1)

N-(4-Methylphenyl)-2-{5-[3-trifluoromethyl)phenyl]-2H-tetrazol-2-yl}acetamide (compound R29A)

The concentrations of the test ompounds causing a 50% inhibition respectively for the two enzymes are presented below

| Compound tested | 15-PGDH (IC50 μM) | PGFS (IC50 μM) |
|---|---|---|
| Compound 4: N-(2-methoxyphenyl)-2-(5-phenyl-2H-tetrazol-2-yl) acetamide | 55 | >75 |

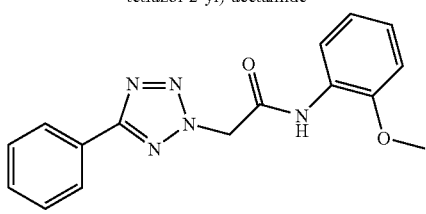

| | | |
|---|---|---|
| Compound R29A: | 30 | >75 |

| Compound tested | 15-PGDH (IC50 μM) | PGFS (IC50 μM) |
|---|---|---|
| N-(4-methylphenyl)-2-{5-[3-(trifluoromethyl)phenyl]-2H-tetrazol-2-yl}acetamide: | | |
| Compound 1: 1-phenyl-2-(2-phenyl-2H-tetrazol-5-yl)ethanone | 40 | >75 |

The test compounds are inhibitors specific for 15-PGDH. In this regard, they will therefore allow a reduction in hair loss, in particular which is natural.

EXAMPLE 6

Demonstration of the Efficacy of a Specific 15-PGDH Inhibitor on a Cellular Model The present study aims to evaluate this selection of compounds in a cellular model. This will provide us with information on the penetration of the active agent into the cytosol and on its efficacy as an inhibitor which is spelective for 15-PGDH under more complex experimental conditions than a simple reaction medium.

Materials and Methods

D-2. Culture of U937 (CRL-1593 American Type Cells Collection) in RPMI 1640 medium+10% foetal calf serum+2 mM L-Glutamine+antibiotics at 37° C. under 5% $CO_2$.

D-1. Preparation of a suspension of U937 ($1\times10^6$ cells/ml) in RPMI 1640 medium+10% foetal calf serum+2 mM Glutamine+Antibiotics+10 nM PMA (phorbol 12-myristate 13-acetate), introduction of 200 μl/well of this suspension into a 96-well plate (3 wells per molecule and per concentration to be tested+corresponding controls). Incubation 36 h 00 min at 37° C. under 5% $CO_2$.

J0. Removal of the supernatants (the cells have adhered: microscope check), and introduction into each well of 100 μl of RPMI 1640+2 mM L-Glutamine+10 ng LPS (except absolute control)+the molecule to be tested at the desired concentration (here 5 and 25 μM).

Incubation for 6 h 00 min at 37° C. under 5% $CO_2$.

The stock solutions of molecules to be tested are at 25 mM in DMSO.

All the wells will contain the same final quantity of DMSO.

Immediate evaluation of the quantity of PGF2α secreted by the cells (50 μl) under different conditions (molecules or controls) using an immunoenzymatic assay kit (Cayman ref. 516011).

Results as % of the LPS control

| Reference Molecule (5 μM) | % of the control |
|---|---|
| Compound 1: 1-phenyl-2-(2-phenyl-2H-tetrazol-5-yl)ethanone | +16 |
| N-(4-methylphenyl)-2-{5-[3-(trifluoromethyl)phenyl]-2H-tetrazol-2-yl}acetamide: | +46 |
| Compound 4: N-(2-methoxyphenyl)-2-(5-phenyl-2H-tetrazol-2-yl)acetamide | +6 |

This confirms that the inhibitors selective for 15-PGDH are effective in a cellular environment and protect prostaglandins.

The compositions below are obtained by the usual techniques commonly used in the cosmetic or pharmaceutical field.

EXAMPLE 7

Hair Lotion

| | |
|---|---|
| Compound 1 | 0.80 g |
| Propylene glycol | 10.00 g |
| Isopropyl alcohol qs | 100.00 g |

This lotion is applied to the scalp, once or twice per day, at the rate of 1 ml per application, by lightly massaging the scalp in order to cause penetration of the active agent. The hair is then dried in the open air. This lotion makes it possible to reduce the loss of hair and to promote its regrowth.

EXAMPLE 8

Hair Lotion

| | |
|---|---|
| Compound 4 | 1.00 g |
| Propylene glycol | 30.00 g |

-continued

| | |
|---|---|
| Ethyl alcohol | 40.00 g |
| Water qs | 100.00 g |

This lotion is applied to the scalp, once or twice per day, at the rate of 1 ml per application, by lightly massaging the scalp in order to cause penetration of the active agent. The hair is then dried in the open air.

The invention claimed is:

1. A method for stimulating or inducing the growth and/or reducing the loss and/or increasing the density and/or reducing the heterogeneity of the diameter of keratinous fibers in a human being in need of same, said method comprising administering an effective amount at least one 15-hydroxyprostaglandin dehydrogenase (15-PGDH) inhibitor, or an effective amount of a composition comprising at least one 15-hydroxyprostaglandin dehydrogenase (15-PGDH) inhibitor and a cosmetically or pharmaceutically acceptable medium, to said human being, wherein said at least one 15-PGDH inhibitor is at least one tetrazole compound of formula (I) or (II):

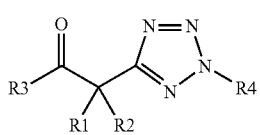
(I)

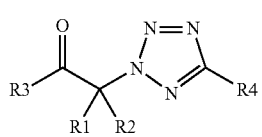
(II)

or an inorganic or organic salt thereof, in which:

each of $R_1$ and $R_2$ is independently hydrogen, halogen, $OR_5$, $SR_5$, $NR_5R'_5$, $COOR_5$, $COR_5$, $CONR_5R'_5$, $CF_3$, $CN$, $NR_5COR'_5$, $SO_2R_5$, $SO_2NR_5R'_5$, $NR_5SO_2R'_5$, $CSR_5$, $OCOR_5$, $COSR_5$, $SCOR_5$, $CSNR_5R'_5$, $NR_5CONR'_5R''_5$, $NR_5C(=NR'_5)NR''_5R'''_5$, $NR_5CSR'_5$, $NR_5CSNR'_5R''_5$, a linear or branched $C_1$-$C_{20}$ alkyl radical, or a ring that is cyclopentyl, cyclohexyl, pyridine, piperidine, morpholine, pyrrole, furan, thiazole, phenyl or naphthyl, each $R_1$ and $R_2$ alkyl radical being saturated or unsaturated, each $R_1$ and $R_2$ alkyl radical and each $R_1$ and $R_2$ ring being optionally substituted with at least one substituent $A_1$, where each of $R_5$, $R'_5$, $R''_5$ and $R'''_5$ independently is hydrogen, a linear or branched $C_1$-$C_{20}$ alkyl radical or a 4- to 7-atom hydrocarbon ring, each $R_5$, $R'_5$, $R''_5$ and $R'''_5$ hydrocarbon ring and each $R_5$, $R'_5$, $R''_5$ and $R'''_5$ alkyl radical being saturated or unsaturated and optionally substituted with at least one substituent $A_2$;

$R_3$ is hydrogen, $OR_6$, $SR_6$, $NR_6R'_6$, $CF_3$, $NR_6COR'_6$, $NR_6SO_2R'_6$, $NR_6CONR'_6R''_6$, $NR_6CSR'_6$, $NR_6CSNR'_6R''_6$, a linear or branched $C_1$-$C_{20}$ alkyl radical, or a ring that is cyclopentyl, cyclohexyl, phenyl or naphthyl, the $R_3$ alkyl radical being saturated or unsaturated, the $R_3$ alkyl radical or the $R_3$ ring being optionally substituted with at least one substituent $A_3$, with each of $R_6$, $R'_6$ and $R''_6$ independently being hydrogen, a linear or branched $C_1$-$C_{20}$ alkyl radical, or a 4- to 7-atom hydrocarbon ring, each $R_6$, $R'_6$ and $R''_6$ alkyl radical and each $R_6$, $R'_6$ and $R''_6$ hydrocarbon ring being saturated or unsaturated and optionally substituted with at least one substituent $A_4$;

$R_4$ is hydrogen, $COOR_7$, $CONR_7R'_7$, $SO_2R_7$, $SO_2NR_7R'_7$, $COR_7$, $CSR_7$, $COSR_7$, $CSNR_7R'_7$, a linear or branched $C_1$-$C_{20}$ alkyl radical, or a ring that is cyclopentyl, cyclohexyl, phenyl or naphthyl, the $R_4$ alkyl radical being saturated or unsaturated, the $R_4$ alkyl radical or the $R_4$ ring being optionally substituted with at least one substituent $A_5$; or $R_4$ additionally represents, in the case of formula (II), halogen, $OR_7$, $SR_7$, $NR_7R'_7$, $CF_3$, CN, $NR_7COR'_7$, $NR_7SO_2R'_7$, $OCOR_7$, $SCOR_7$, $NR_7CONR'_7R''_7$, $NR_7C(=NR'_7)NR''_7R'''_7$, $NR_7CSR'_7$ or $NR_7CSNR'_7R''_7$, with $R_7$, $R'_7$, $R''_7$ and $R'''_7$ independently being hydrogen, a linear or branched $C_1$-$C_{20}$ alkyl radical, or a 4- to 7-atom hydrocarbon ring, each $R_7$, $R'_7$, $R''_7$ and $R'''_7$ alkyl radical and each $R_7$, $R'_7$, $R''_7$ and $R'''_7$ hydrocarbon ring being saturated or unsaturated and optionally substituted with at least one substituent $A_6$;

each of $A_1$ and $A_2$ independently is halogen, a heterocycle having from 4 to 7 atoms and at least one hetero ring atom, $OR_8$, $SR_8$, $NR_8R'_8$, $COOR_8$, $CONR_8R'_8$, $CF_3$, CN, $NR_8COR'_8$, $SO_2R_8$, $SO_2NR_8R'_8$, $NR_8SO_2R'_8$, $COR_8$, $CSR_8$, $OCOR_8$, $COSR_8$, $SCOR_8$, $CSNR_8R'_8$, $NR_8CONR'_8R''_8$, $NR_8C(=NR'_8)NR''_8R'''_8$, $NR_8CSR'_8$, or $NR_8CSNR'_8R''_8$;

each of $A_3$ and $A_4$ independently is halogen, $R_9$, $OR_9$, $SR_9$, $NR_9R'_9$, $COOR_9$, $CONR_9R'_9$, $CF_3$, CN, $NR_9COR'_9$, $SO_2R_9$, $SO_2NR_9R'_9$, $NR_9SO_2R'_9$, $CSR_9$, $OCOR_9$, $COSR_9$, $SCOR_9$, $CSNR_9R'_9$, $NR_9CONR'_9R''_9$, $NR_9C(=NR'_9)NR''_9R'''_9$, $NR_9CSR'_9$, or $NR_9CSNR'_9R''_9$;

each of $A_5$ and $A_6$ is independently halogen, $R_{10}$, $OR_{10}$, $SR_{10}$, $NR_{10}R'_{10}$, $CF_3$, CN, $NR_{10}COR'_{10}$, $SO_2R_{10}$, $SO_2NR_{10}R'_{10}$, $NR_{10}SO_2R'_{10}$, $CSR_{10}$, $OCOR_{10}$, $SCOR_{10}$, $CSNR_{10}R'_{10}$, $NR_{10}CONR'_{10}R''_{10}$, $NR_{10}C(=NR'_{10})NR''_{10}R'''_{10}$, $NR_{10}CSR'_{10}$, and $NR_{10}CSNR'_{10}R''_{10}$; and each of $R_8$, $R'_8$, $R''_8$, $R'''_8$, $R_9$, $R'_9$, $R''_9$, $R'''_9$, $R_{10}$, $R'_{10}$, $R''_{10}$ and $R'''_{10}$ independently is hydrogen, a saturated or unsaturated, linear or branched $C_1$-$C_{20}$ alkyl radical, a saturated or unsaturated 4- to 7-atom hydrocarbon ring, or a benzyl radical.

2. A method according to claim 1, wherein in said at least one compound of formula (I) or (II):

each of $R_1$ and $R_2$ is independently hydrogen, halogen, $OR_5$, $SR_5$, $NR_5R'_5$, $COOR_5$, $CF_3$, CN, linear or branched $C_1$-$C_{20}$ alkyl radical, or a ring that is cyclopentyl, cyclohexyl, pyridine, piperidine, morpholine, pyrrole, furan, thiazole, phenyl or naphthyl, each $R_1$ and $R_2$ alkyl radical being saturated or unsaturated, where each of $R_5$ and $R'_5$ independently is hydrogen, a linear or branched $C_1$-$C_{20}$ alkyl radical, or a 4- to 7-atom hydrocarbon ring, each $R_5$ and $R'_5$ hydrocarbon ring and each $R_5$ and $R'_5$ alkyl radical being saturated or unsaturated;

$R_3$ is hydrogen, $OR_6$, $SR_6$, $NR_6R'_6$, $CF_3$, linear or branched $C_1$-$C_{20}$ alkyl radical, or a ring that is cyclopentyl, cyclohexyl, phenyl or naphthyl, the $R_3$ alkyl radical being saturated or unsaturated, the $R_3$ alkyl radical or the $R_3$ ring being optionally substituted with at least one substituent $A_3$, with each of $R_6$ and $R'_6$ independently being hydrogen, a linear or branched $C_1$-$C_{20}$ alkyl radical, or a 4- to 7-atom hydrocarbon ring, each $R_6$, $R'_6$ and $R''_6$ alkyl radical and each $R_6$, $R'_6$ and $R''_6$ hydrocarbon ring being saturated or unsaturated and optionally substituted with at least one substituent $A_4$;

$R_4$ is hydrogen, $COOR_7$, $CSR_7$, a linear or branched $C_1$-$C_{20}$ alkyl radical, or a ring that is cyclopentyl, cyclohexyl, phenyl or naphthyl, the $R_4$ alkyl radical being saturated or unsaturated; or $R_4$ additionally represents, in the case of formula (II), halogen, $OR_7$, $SR_7$, $NR_7R'_7$, $CF_3$, CN, with $R_7$ and $R'_7$ independently being hydrogen, a linear or branched $C_1$-$C_{20}$ alkyl radical, or a 4- to 7-atom hydrocarbon ring, each $R_7$ and $R'_7$ alkyl radical and each $R_7$ and $R'_7$ hydrocarbon ring being saturated or unsaturated, optionally substituted with at least one substituent selected from the group consisting of $OR_{10}$, $SR_{10}$, $NR_{10}R'_{10}$, and $CF_3$, with each of $R_{10}$ and $R'_{10}$ being a saturated or unsaturated, linear or branched $C_1$-$C_{20}$ alkyl radical; and each of $A_3$ and $A_4$ is independently halogen, $R_9$, $OR_9$, $SR_9$, $NR_9R'_9$, $COOR_9$, or $CF_3$, with $R_9$ and $R'_9$ independently being hydrogen, a saturated or unsaturated, linear or branched $C_1$-$C_{20}$ alkyl radical, a saturated or unsaturated 4- to 7-atom hydrocarbon ring, or a benzyl radical.

3. A method according to claim 1, wherein in said at least one compound of formula (I) or (II):

$R_3$ is hydrogen, $OR_6$, $SR_6$, $NR_6R'_6$, $CF_3$, a linear or branched $C_1$-$C_{20}$ alkyl radical, or a ring that is cyclopentyl, cyclohexyl, phenyl or naphthyl, the $R_3$ alkyl radical being saturated or unsaturated and, the $R_3$ alkyl radical or the $R_3$ ring being optionally substituted with at least one substituent $A_3$, with each of $R_6$ and $R'_6$ independently being hydrogen, a linear or branched $C_1$-$C_{20}$ alkyl radical, or a 4- to 7-atom hydrocarbon ring, each $R_6$ and $R'_6$ alkyl radical and each $R_6$ and $R'_6$ hydrocarbon ring being saturated or unsaturated and optionally substituted with at least one substituent $A_4$;

$R_4$ is hydrogen, a linear or branched $C_1$-$C_{20}$ alkyl radical, or a ring that is cyclopentyl, cyclohexyl, phenyl or naphthyl, the $R_4$ alkyl radical being saturated or unsaturated, the $R_4$ alkyl radical or the $R_4$ ring being optionally substituted with at least one substituent selected from the group consisting of $OR_{10}$, $SR_{10}$, $NR_{10}R'_{10}$, and $CF_3$, with each of $R_{10}$ and $R'_{10}$ being a saturated or unsaturated, linear or branched $C_1$-$C_{20}$ alkyl radical; and each of $A_3$ and $A_4$ is independently $R_9$, $OR_9$, $SR_9$, $NR_9R'_9$, or $COOR_9$, with each of $R_9$ and $R'_9$ independently being hydrogen, a saturated or unsaturated, linear or branched $C_1$-$C_{20}$ alkyl radical, a saturated or unsaturated 4- to 7-atom hydrocarbon ring, or a benzyl radical.

4. A method according to claim 1, wherein at least one of $R_1$ and $R_2$ is hydrogen or halogen.

5. A method according to claim 2, wherein at least one of $R_1$ and $R_2$ is hydrogen or halogen.

6. A method according to claims 3, wherein at least one of $R_1$ and $R_2$ is hydrogen or halogen.

7. A method according to claim 1, wherein $R_3$ is $NR_6R'_6$ or an aryl radical optionally substituted with one $A_3$ substituent.

8. A method according to claim 2, wherein $R_3$ is $NR_6R'_6$ or an aryl radical optionally substituted with one $A_3$ substituent.

9. A method according to claim 3, wherein $R_3$ is $NR_6R'_6$ or an aryl radical optionally substituted with one $A_3$ substituent.

10. A method according to claim 1, wherein $R_3$ is naphthyl or phenyl optionally substituted with $OR_9$.

11. A method according to claim 2, wherein $R_3$ is naphthyl or phenyl optionally substituted with $OR_9$.

12. A method according to claim 3, wherein $R_3$ is naphthyl or phenyl optionally substituted with $OR_9$.

13. A method according to claim 10, wherein $R_4$ is naphthyl or phenyl.

14. A method according to claim 11, wherein $R_4$ is naphthyl or phenyl.

15. A method according to claim 12, wherein $R_4$ is naphthyl or phenyl.

16. A method according to claim 1, wherein $R_6$ is hydrogen and $R'_6$ is phenyl, optionally substituted with $OR_9$.

17. A method according to claim 2, wherein $R_6$ is hydrogen and $R'_6$ is phenyl, optionally substituted with $OR_9$.

18. A method according to claim 3, wherein $R_6$ is hydrogen and $R'_6$ is phenyl, optionally substituted with $OR_9$.

19. A method according to claim 1, wherein $R_9$ is saturated, linear or branched $C_1$-$C_{10}$ alkyl.

20. A method according to claim 2, wherein $R_9$ is saturated, linear or branched $C_1$-$C_{10}$ alkyl.

21. A method according to claim 3, wherein $R_9$ is saturated, linear or branched $C_1$-$C_{10}$ alkyl.

22. A method for stimulating or inducing the growth and/or reducing the loss and/or increasing the density and/or reducing the heterogeneity of the diameter of keratinous fibers in a human being, said method comprising administering an effective amount of at least one 15-hydroxyprostaglandin dehydrogenase (15-PGDH) inhibitor, or an effective amount of a composition comprising at least one 15-hydroxyprostaglandin dehydrogenase (15-PGDH) inhibitor and a cosmetically or pharmaceutically acceptable medium, to said human being, wherein said at least one 15-PGDH inhibitor is at least one tetrazole compound of formula (I) or (II):

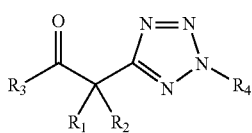

(I)

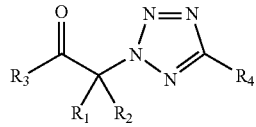

(II)

or an inorganic or organic salt thereof, wherein each of $R_1$ and $R_2$ is hydrogen or halogen; $R_3$ is $NR_6R'_6$, or $R_3$ is naphthyl or phenyl optionally substituted with $OR_9$; $R_4$ is naphthyl or phenyl, optionally substituted with $OCH_3$ or $CF_3$; $R_6$ is hydrogen; $R'_6$ is phenyl optionally substituted with $OR_9$; and $R_9$ is saturated, linear or branched $C_1$-$C_{10}$ alkyl.

23. A method according to claim 1, wherein the salt of the compound of formula (I) or (II) is a sodium or potassium salt, a zinc ($Zn^{2+}$), calcium ($Ca^{2+}$), copper ($Cu^{2+}$), iron ($Fe^{2+}$), strontium ($Sr^{2+}$), magnesium ($Mg^{2+}$), or manganese ($Mn^{2+}$) salt, a triethanolamine, monoethanolamine, diethanolamine, hexadecylamine, N,N,N',N'-tetrakis(2-hydroxypropyl)ethylenediamine or tris-hydroxymethylaminomethane salt, or a hydroxide or carbonate.

24. A method according to claim 2, wherein the salt of the compound of formula (I) or (II) is a sodium or potassium salt, a zinc ($Zn^{2+}$), calcium ($Ca^{2+}$), copper ($Cu^{2+}$), iron ($Fe^{2+}$), strontium ($Sr^{2+}$), magnesium ($Mg^{2+}$), or manganese ($Mn^{2+}$) salt, a triethanolamine, monoethanolamine, diethanolamine, hexadecylamine, N,N,N',N'-tetrakis(2-hydroxypropyl)ethylenediamine or tris-hydroxymethylaminomethane salt, or a hydroxide or carbonate.

25. A method according to claim 3, wherein the salt of the compound of formula (I) or (II) is a sodium or potassium salt, a zinc ($Zn^{2+}$), calcium ($Ca^{2+}$), copper ($Cu^{2+}$), iron ($Fe^{2+}$), strontium ($Sr^{2+}$), magnesium ($Mg^{2+}$), or manganese ($Mn^{2+}$) salt, a triethanolamine, monoethanolamine, diethanolamine, hexadecylamine, N,N,N',N'-tetrakis(2-hydroxypropyl)ethylenediamine or tris-hydroxymethylaminomethane salt, or a hydroxide or carbonate.

26. A method according to claim 22, wherein the salt of the compound of formula (I) or (II) is a sodium or potassium salt, a zinc ($Zn^{2+}$), calcium ($Ca^{2+}$), copper ($Cu^{2+}$), iron ($Fe^{2+}$), strontium ($Sr^{2+}$), magnesium ($Mg^{2+}$), or manganese ($Mn^{2+}$) salt, a triethanolamine, monoethanolamine, diethanolamine, hexadecylamine, N,N,N',N'-tetrakis(2-hydroxypropyl)ethylenediamine or tris-hydroxymethylaminomethane salt, or a hydroxide or carbonate.

27. A method according to claim 22, wherein the compound of formula (I) or (II) is:

1-phenyl-2-(2-phenyl-2H-tetrazol-5-yl)ethanone having the formula:

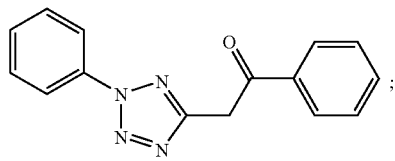

1-(2-methoxyphenyl)-2-(2-phenyl-2H-tetrazol-5-yl)ethanone having the formula:

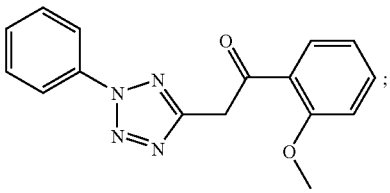

N-(4-methylphenyl)-2-{5-[3-(trifluoromethyl)phenyl]-2H-tetrazol-2-yl}acetamide having the formula:

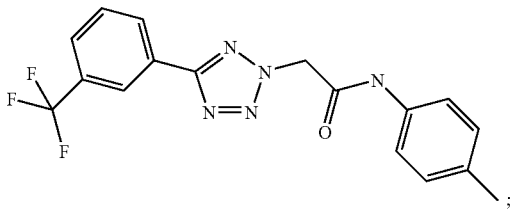

N-(2-phenyl)-2-(5-phenyl-2H-tetrazol-2-yl)acetamide having the formula:

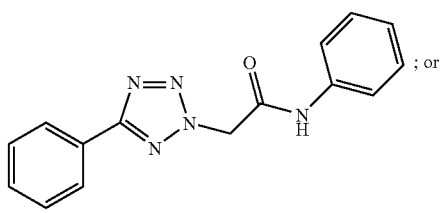

N-(2-methoxyphenyl)-2-(5-phenyl-2H-tetrazol-2-yl)acetamide having the formula:

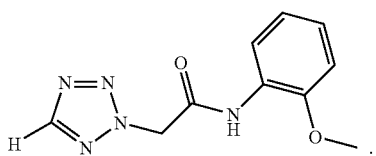

28. A method according to claim 1, wherein the keratinous fibers are selected from head hair, body hair and eyelashes.

29. A method according to claim 2, wherein the keratinous fibers are selected from head hair, body hair and eyelashes.

30. A method according to claim 3, wherein the keratinous fibers are selected from head hair, body hair and eyelashes.

31. A method according to claim 22, wherein the keratinous fibers are selected from head hair, body hair and eyelashes.

32. A method according to claim 27, wherein the keratinous fibers are selected from head hair, body hair and eyelashes.

33. A method according to claim 1, wherein said at least one 15-PGDH inhibitor or composition is applied topically.

34. A method according to claim 2, wherein said at least one 15-PGDH inhibitor or composition is applied topically.

35. A method according to claim 3, wherein said at least one 15-PGDH inhibitor or composition is applied topically.

36. A method according to claim 22, wherein said at least one 15-PGDH inhibitor or composition is applied topically.

37. A method according to claim 27, wherein said at least one 15-PGDH inhibitor or composition is applied topically.

38. A method according to claim 28, wherein said at least one 15-PGDH inhibitor or composition is applied topically.

39. A method according to claim 29, wherein said at least one 15-PGDH inhibitor or composition is applied topically.

40. A method according to claim 30, wherein said at least one 15-PGDH inhibitor or composition is applied topically.

41. A method according to claim 31, wherein said at least one 15-PGDH inhibitor or composition is applied topically.

42. A method according to claim 32, wherein said at least one 15-PGDH inhibitor or composition is applied topically.

43. A method according to claim 1, wherein the 15-PGDH inhibitor is an inhibitor specific for 15-PGDH.

44. A method according to claim 2, wherein the 15-PGDH inhibitor is an inhibitor specific for 15-PGDH.

45. A method according to claim 3, wherein the 15-PGDH inhibitor is an inhibitor specific for 15-PGDH.

46. A method according to claim 22, wherein the 15-PGDH inhibitor is an inhibitor specific for 15-PGDH.

47. A method according to claim 27, wherein the 15-PGDH inhibitor is an inhibitor specific for 15-PGDH.

48. A method according to claim 43, wherein the ratio between the 15-PGDH inhibiting activity and the prostaglandin F synthase (PGF synthase) inhibiting activity is greater than 1.

49. A method according to claim 44, wherein the ratio between the 15-PGDH inhibiting activity and the prostaglandin F synthase (PGF synthase) inhibiting activity is greater than 1.

50. A method according to claim 45, wherein the ratio between the 15-PGDH inhibiting activity and the prostaglandin F synthase (PGF synthase) inhibiting activity is greater than 1.

51. A method according to claim 46, wherein the ratio between the 15-PGDH inhibiting activity and the prostaglandin F synthase (PGF synthase) inhibiting activity is greater than 1.

52. A method according to claim 47, wherein the ratio between the 15-PGDH inhibiting activity and the prostaglandin F synthase (PGF synthase) inhibiting activity is greater than 1.

* * * * *